(12) United States Patent
Naldini et al.

(10) Patent No.: US 10,617,721 B2
(45) Date of Patent: Apr. 14, 2020

(54) METHODS FOR GENETIC MODIFICATION OF STEM CELLS

(71) Applicants: Ospedale San Raffaele S.R.L., Milan (IT); Fondazione Telethon, Rome (IT)

(72) Inventors: Luigi Naldini, Milan (IT); Bernhard Rudolf Gentner, Milan (IT); Erika Zonari, Milan (IT); Francesco Boccalatte, Milan (IT)

(73) Assignees: OSPEDALE SAN RAFFAELE S.R.L., Milan (IT); FONDAZIONE TELETHON, Rome (IT)

(*) Notice: Subject to any disclaimer, the term of this patent is extended or adjusted under 35 U.S.C. 154(b) by 673 days.

(21) Appl. No.: 15/031,169

(22) PCT Filed: Oct. 24, 2014

(86) PCT No.: PCT/IB2014/065594
§ 371 (c)(1),
(2) Date: Apr. 21, 2016

(87) PCT Pub. No.: WO2015/059674
PCT Pub. Date: Apr. 30, 2015

(65) Prior Publication Data
US 2016/0256492 A1 Sep. 8, 2016

(30) Foreign Application Priority Data

Oct. 24, 2013 (GB) .................................. 1318830.5
May 21, 2014 (GB) .................................. 1409067.4

(51) Int. Cl.
*A61K 35/28* (2015.01)
*C12N 5/0789* (2010.01)
*C12N 15/86* (2006.01)
*A61K 48/00* (2006.01)
*C12N 7/00* (2006.01)

(52) U.S. Cl.
CPC .......... *A61K 35/28* (2013.01); *A61K 48/0091* (2013.01); *C12N 5/0647* (2013.01); *C12N 15/86* (2013.01); *C12N 7/00* (2013.01); *C12N 2510/00* (2013.01); *C12N 2740/15043* (2013.01)

(58) Field of Classification Search
CPC .... A61K 35/28; A61K 48/0091; C12N 15/86; C12N 5/0647; C12N 2510/00; C12N 7/00; C12N 2740/15043
USPC .......................... 424/93.21, 93.2, 93.7, 577
See application file for complete search history.

(56) References Cited

U.S. PATENT DOCUMENTS

| 4,797,368 A | 1/1989 | Carter et al. |
| 5,139,941 A | 8/1992 | Muzyczka et al. |
| 5,840,580 A | 11/1998 | Terstappen et al. |
| 6,006,633 A | 12/1999 | Kaiser et al. |
| 2001/0051375 A1 | 12/2001 | Kelly et al. |
| 2002/0159984 A1 | 10/2002 | Brown |
| 2006/0003452 A1 | 1/2006 | Humeau et al. |
| 2006/0046268 A1 | 3/2006 | Devore et al. |
| 2009/0191164 A1 | 7/2009 | Majeti |
| 2010/0197015 A1 | 8/2010 | Reid et al. |
| 2010/0266556 A1 | 10/2010 | Nishino et al. |
| 2011/0091426 A1 | 4/2011 | Chute et al. |
| 2013/0079424 A1 | 3/2013 | Gerber |

FOREIGN PATENT DOCUMENTS

| AR | 0071353 | 6/2010 |
| CN | 101706507 | 5/2010 |
| CN | 101735979 | 6/2010 |
| CN | 101831434 | 9/2010 |
| CN | 102220282 | 10/2011 |
| CN | 103018463 | 4/2013 |
| CN | 103403151 | 11/2013 |
| EP | 0455482 | 11/1991 |
| EP | 0610774 | 8/1994 |
| EP | 0662512 | 7/1995 |
| EP | 0708336 | 4/1996 |
| EP | 1312668 | 5/2003 |
| EP | 1593737 | 11/2005 |
| EP | 1366144 | 8/2009 |
| EP | 2206773 | 7/2010 |
| EP | 2417984 | 2/2012 |
| EP | 2615166 | 7/2013 |
| FR | 2891551 | 4/2007 |
| JP | 2001-503976 | 3/2001 |
| JP | 2006061106 | 3/2006 |
| JP | 2012-507554 | 3/2012 |
| JP | 2012-525141 | 10/2012 |
| JP | 2005-517402 | 6/2015 |
| KR | 20050090542 | 9/2005 |
| KR | 100702862 | 3/2007 |

(Continued)

OTHER PUBLICATIONS

Byk et al. (2005) Stem Cells, vol. 23, 561-574.*
Ahmed et al., "Impaired bone marrow homing of cytokine-activated Cd34+ cells in the NOD/SCID model." Blood 103 (6):2079-87 (Mar. 2004; Epub Nov. 2003).
Aiuti et al., "Lentiviral hematopoetic stem cell gene therapy in patients with Wiskott-Aldrich syndrome." Science 341(6148)1233151 (Aug. 2013).
Baldwin et al., "Increasing transduction efficiency in human hematopoietic stem cells for gene therapy," Blood 120:2052 (Abstract 2052, 2012).

(Continued)

*Primary Examiner* — Anne Marie S Wehbe
(74) *Attorney, Agent, or Firm* — McDonnell Boehnen Hulbert & Berghoff LLP

(57) ABSTRACT

A method of preparing a therapeutic cell population for clinical use from a starting population of cells comprising haematopoietic stem cells, said method comprising separating a population of cells that substantially do not express CD38 but which express CD34 from the starting population of cells, and transducing the separated cell population with a vector to obtain the therapeutic cell population.

23 Claims, 15 Drawing Sheets

(56) References Cited

FOREIGN PATENT DOCUMENTS

| | | |
|---|---|---|
| KR | 100773253 | 11/2007 |
| KR | 20130028294 | 3/2013 |
| NZ | 541541 | 4/2007 |
| WO | WO 1993/025216 | 12/1993 |
| WO | WO 95/12813 | 5/1995 |
| WO | WO 1998/005635 | 2/1998 |
| WO | WO 1998/007859 | 2/1998 |
| WO | WO 1998/009985 | 3/1998 |
| WO | WO 1998/015615 | 4/1998 |
| WO | WO 1998/017815 | 4/1998 |
| WO | WO 1999/023205 | 5/1999 |
| WO | WO 00/36090 | 6/2000 |
| WO | WO 2000/034495 | 6/2000 |
| WO | WO 2000/043498 | 7/2000 |
| WO | WO 2001/027304 | 4/2001 |
| WO | WO 01/66150 * | 9/2001 |
| WO | WO 2001/066150 | 9/2001 |
| WO | WO 2001/079518 | 10/2001 |
| WO | WO 2003/060138 | 7/2003 |
| WO | WO 2003/068937 | 8/2003 |
| WO | WO 2004/071464 | 8/2004 |
| WO | WO 2004/072264 | 8/2004 |
| WO | WO 2005/083061 | 9/2005 |
| WO | WO 2006/081435 | 8/2006 |
| WO | WO 2006/093857 | 9/2006 |
| WO | WO 2006/093858 | 9/2006 |
| WO | WO 2006/093860 | 9/2006 |
| WO | WO 2006/093881 | 9/2006 |
| WO | WO 2007/071994 | 6/2007 |
| WO | WO 2008/136656 | 11/2008 |
| WO | WO 2008/136670 | 11/2008 |
| WO | WO 2009/072635 | 6/2009 |
| WO | WO 2010/059401 | 5/2010 |
| WO | WO 2010/125471 | 11/2010 |
| WO | WO 2012/008733 | 1/2012 |
| WO | WO 2012/094193 | 7/2012 |
| WO | WO 2013/049615 * | 4/2013 |
| WO | WO 2013/077639 | 5/2013 |
| WO | WO 2013/085303 | 6/2013 |

OTHER PUBLICATIONS

Biffi et al., "Lentiviral hematopoetic stem cell gene therapy benefits metachromatic leukodystrophy." Science 341(6148)1233158 (Aug. 2013).

Boitano et al., "Aryl hydrocarbon receptor antagonists promote the expansion of human hematopoietic stem cells." Science 329(5997):1345-8. (Sep. 2010; Epub Aug. 2010).

Cartier et al., "Hematopoietic stem cell gene therapy with a lentiviral vector in X-linked adrenoleukodystrophy." Science 326(5954):818-23 (Nov. 2009).

Cavazzana-Calvo et al., "Transfusion independence and HMGA2 activation after gene therapy of human β-thalassaemia." Nature 467(7313):318-22 (Sep. 2010).

Coffin et al. "Retroviruses", Cold Spring Harbour Laboratory Press Eds: JM Coffin, SM Hughes, HE Varmus pp. 758-763 (1997).

Csaszar et al., "Rapid expansion of human hematopoietic stem cells by automated control of inhibitory feedback signaling." Cell Stem Cell 10(2):218-29 (Feb. 2010).

Deglon et al., "Self-inactivating lentiviral vectors with enhanced transgene expression as potential gene transfer system in Parkinson's disease." Human Gene Therapy 11(1);179-90 (Jan. 2000).

Delaney et al., "Notch-mediated expansion of human cord blood progenitor cells capable of rapid myeloid reconstitution." Nat Med. 16(2):232-36 (Feb. 2010; Epub Jan. 2010).

Derse et al., "Mutagenesis of EIAV TAT reveals structural fatures essential for transcriptional activation and TAR element recognition." Virology 194(2);530-36 (Jun. 1993).

Doty et al., "An all-feline retroviral packaging system for transduction of human cells" Human Gene Therapy 21:1019-27 (Aug. 2010).

Dumais et al., "Prostaglandin E2 up-regulates HIV-1 long terminal repeats-driven gene activity in T cells via NF-kappaB-dependent and -independent signaling pathways." J Biol Chem. 273(42);27306-14 (Oct. 1998).

Gait et al., "Oligonucleotide Synthesis: A Practical Approach." FEBS Letters 188(1);166-67 (1984).

Gentner et al., "Stable Knockdown of microRNA in vivo by lentiviral vectors." Nat Methods 6(1):63-66 (Jan. 2009; Epub Nov. 2008).

Glimm et al., "Evidence of similar effects of short-term culture on the initial repopulating activity of mobilized peripheral blood transplants assessed in NOD/SCID-beta2microglobulin (null) mice and in autografted patients." Exp Hematol. 33(1):20-25 (Jan. 2005).

Goessling et al., "Prostaglandin E2 enhances human cord blood stem cell xenotransplants and shows long-term safety in preclinical nonhuman primate transplant models." Cell Stem Cell 8(4);445-58 (Apr. 2011).

Guenechea et al., "Delayed engraftment of nonobese diabetic/severe combined immunodeficient mice transplanted with ex vivo-expanded human CD34(+) cord blood cells." Blood 93(3):1097-1105 (Feb. 1999).

Himburg et al., "Pleiotrophin regulates the expansion and regeneration of hematopoietic stem cells." Nat Med. 16(4):475-82 (Apr. 2010; Epub Mar. 2010).

Hoggatt et al. "Differential stem-and progenitor-cell trafficking by prostaglandin E2." Nature 495(7441);365-69 (Mar. 2013).

Horn et al., "Lentivirus-mediated gene transfer into hematopoietic repopulating cells in baboons." Gene Therapy 9 (21);1464-71 (Nov. 2002).

Iwakuma et al. "Self-inactivating lentiviral vectors with U3 and U5 modifications." Virol. 261(1);120-32 (Aug. 1999).

Kallinikou et al., "Engraftment defect of cytokine-cultured adult human mobilized CD34(+) cells is related to reduced adhesion to bone marrow niche elements." Br. J. Haematol. 158(6):778-87 (Sep. 2012; Epub Jul. 2012).

Lewis et al., "Passage through mitosis is required for oncoretroviruses but not for human immunodeficiency virus." J Virol. 68(1);510-16 (Jan. 1994).

Lewis et al., "Human immunodeficiency virus infection of cells arrested in the cell cycle." EMBO J. 11(8);3053-58 (Aug. 1992).

Martarano et al., "Equine infectious anemia virus trans-regulatory protein Rev controls viral mRNA stability, accumulation, and alternative splicing." J Virol. 68(5);3102-11 (May 1994).

Marty et al., "MoMuLV-derived self-inactivating retroviral vectors possessing multiple cloning sites and expressing the resistance to either G418 or hygromycin B," Biochimie 72(12):885-87 (1990).

Maury et al., "Cellular and viral specificity of equine infectious anemia virus Tat transactivation." Virology 200 (2);632-42 (May 1994).

Mazurier et al., "Lentivector-mediated clonal tracking reveals intrinsic heterogeneity in the human hematopoietic stem cell compartment and culture-induced stem cell impairment." Blood 103(2):545-52 (Jan. 2004).

Naviaux et al., "The pCL vector system: rapid production of helper-free, high-titer, recombinant retroviruses." J. Virol. 70(8);5701-05(Aug. 1996).

Ng et al., "Selective in vitro expansion and efficientretroviral transduction of human CD34+ CD38− haematopoietic stem cells" British Journal Haematology, 117:226-37 (2002).

Pelus et al., "Pleiotropic effects of prostaglandin E2 in hematopoiesis; prostaglandin E2 and other eicosanoids regulate hematopoietic stem and progenitor cell function." Prostaglandins Other Lipid Mediat 96(1-4);3-9 (Nov. 2011; Epub Jun. 2011).

Reitsma et al., "Method for purification of human hematopoietic stem cells by flow cytometry" from Methods in Molecular Medicine vol. 63, pp. 59-77 (2002).

Santat et al., "Recombinant AAV2 transduction of primitive human hematopoietic stem cells capable of serial engraftment in immune-deficient mice," Proc Natl Acad Sci, 102(31):11053-58 (Aug. 2005).

Scaramuzza et al., "Preclinical safety and efficacy of human CD34(+) cells transduced with lentiviral vector for the treatment of Wiskott-Aldrich syndrome" Mol Ther. 21(1);175-84 (Jan. 2013; Epub Feb. 2012).

(56) References Cited

OTHER PUBLICATIONS

Walasek et al., "Hematopoietic stem cell expansion: challenges and opportunities." Ann N.Y. Acad Sci.1266:138-50 (Aug. 2012).

Woods et al., "Lentiviral-mediated gene transfer into haematopoietic stem cells." J. Intern Med. 249(4);339-43(Apr. 2001).

Xu et al., "Umbilical cord blood progeny cells that retain a CD34+ phenotype after ex-vivo expansion have less engraftment potential than unexpanded CD34+ cells." Transfusion 41(2):213-18 (Feb. 2001).

Yu et al., "Self-inactivating retroviral vectors designed for transfer of whole genes into mammalian cells." PNAS 83(10);3194-98(May 1996).

Zhang et al., "Angiopoietin-like 5 and IGFBP2 stimulate ex vivo expansion of human cord blood hematopoietic stem cells as assayed by NOD/SCID transplantation." Blood 111(7):3415-23 (Apr. 2008; Epub Jan. 2008).

\* cited by examiner

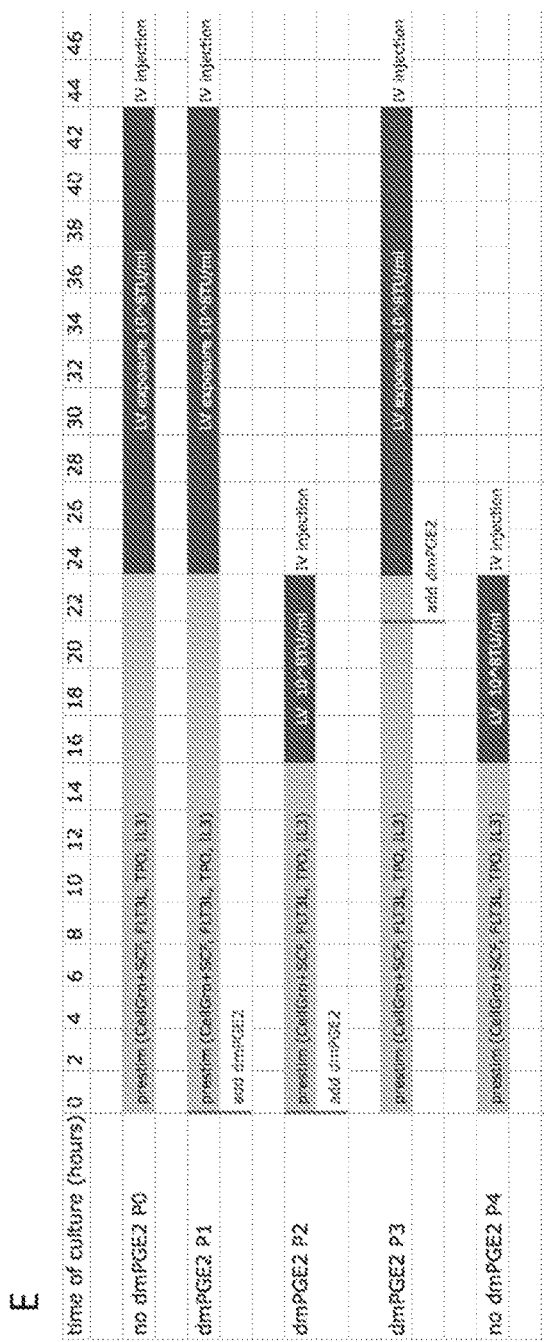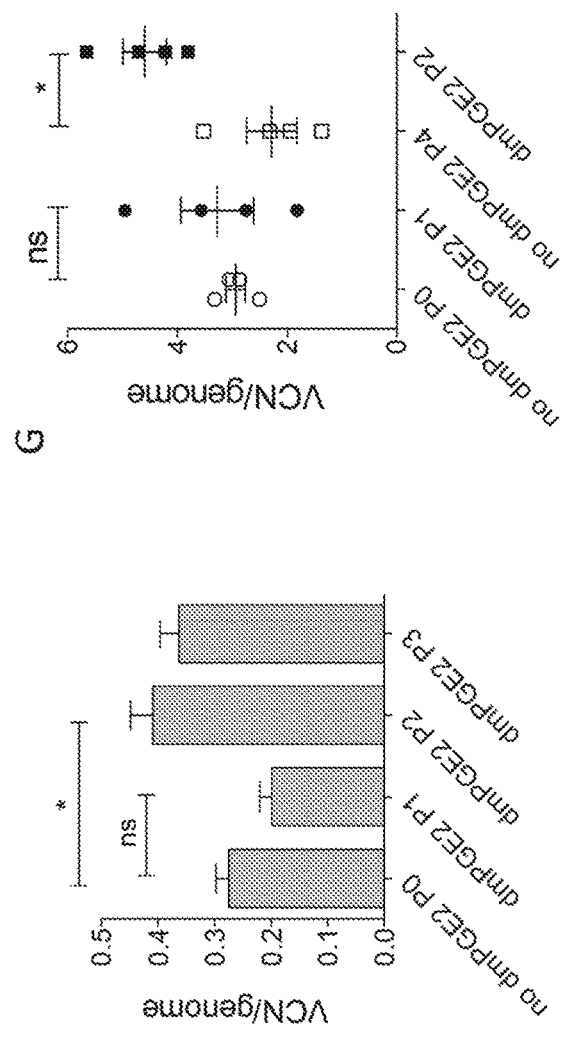
FIGURES 5E-5G

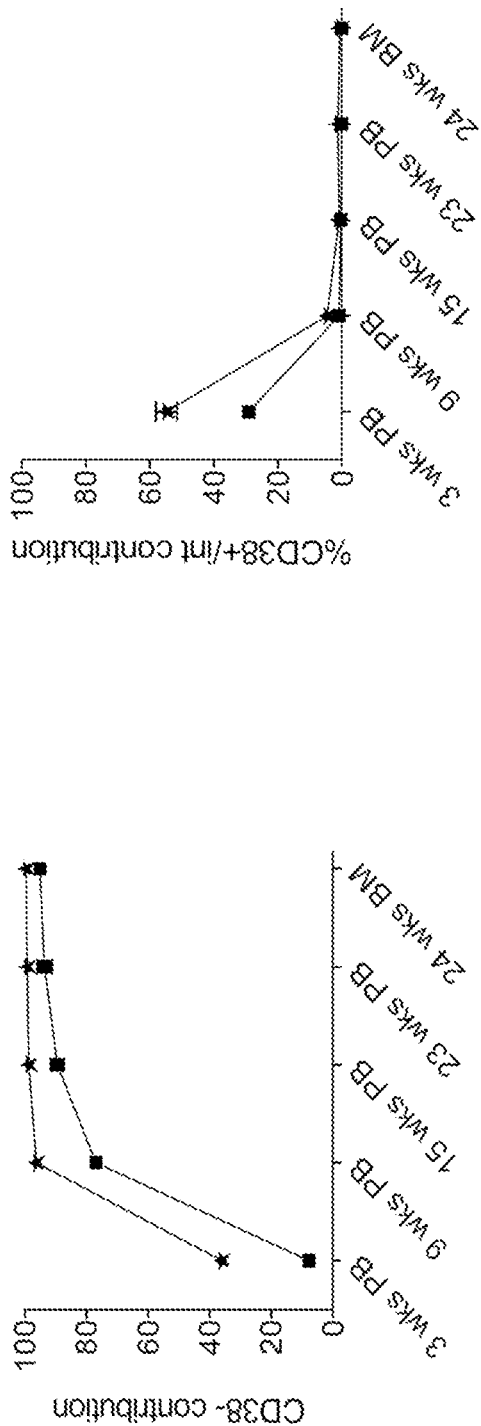
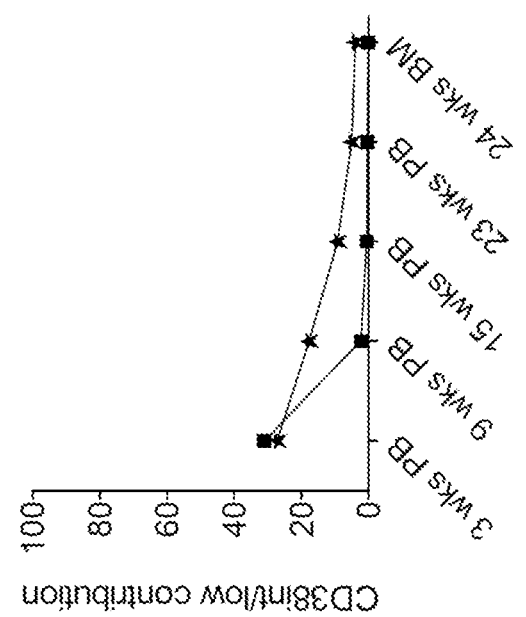
FIGURE 8A
FIGURE 8B
FIGURE 8C

METHODS FOR GENETIC MODIFICATION OF STEM CELLS

This application is a national stage application under 35 U.S.C. § 371 of International Application No. PCT/IB2014/065594, filed Oct. 24, 2014, which claims the benefit of United Kingdom Application No. GB 1318830.5, filed Oct. 24, 2013, as well as the benefit of United Kingdom Application No. GB 1409067.4, filed May 21, 2014, the disclosures of each of which are explicitly incorporated by reference herein.

FIELD OF THE INVENTION

The present invention relates to haematopoietic stem cells (HSCs) and haematopoietic progenitor cells. More specifically, the present invention relates to improved methods for the genetic modification of HSCs. The present invention also relates to improved methods for the use of genetically modified haematopoietic stem and progenitor cells in gene therapy.

BACKGROUND TO THE INVENTION

The haematopoietic system is a complex hierarchy of cells of different mature cell lineages. These include cells of the immune system that offer protection from pathogens, cells that carry oxygen through the body and cells involved in wound healing. All these mature cells are derived from a pool of haematopoietic stem cells (HSCs) that are capable of self-renewal and differentiation into any blood cell lineage.

As HSCs have the ability to replenish the entire haematopoietic system, they may be used for transplantations, for example following haematotoxic insults such as radiotherapy or chemotherapy, or for the replacement of leukaemic cells.

Hematopoietic cell transplantation (HCT) is a curative therapy for several inherited and acquired disorders. However, allogeneic HCT is limited by the poor availability of matched donors, and the mortality associated with the allogeneic procedure which is mostly related to graft-versus-host disease (GvHD) and infectious complications provoked by the profound and long-lasting state of immune dysfunction.

Gene therapy approaches based on the transplantation of genetically modified autologous HSCs offer potentially improved safety and efficacy over allogeneic HCT. They are particularly relevant for patients lacking a matched donor.

The concept of stem cell gene therapy is based on the genetic modification of a relatively small number of stem cells. These persist long-term in the body by undergoing self-renewal, and generate large numbers of genetically "corrected" progeny. This ensures a continuous supply of corrected cells for the rest of the patient's lifetime. HSCs are particularly attractive targets for gene therapy since their genetic modification will be passed to all the blood cell lineages as they differentiate. Furthermore, HSCs can be easily and safely obtained, for example from bone marrow, mobilised peripheral blood and umbilical cord blood.

Efficient long-term gene modification of HSCs and their progeny requires a technology which permits stable integration of the corrective DNA into the genome, without affecting HSC function.

Long-term benefit requires the transplantation of a sufficiently high number of modified HSCs, which can repopulate the conditioned bone marrow, giving rise to corrected blood cells of all hematopoietic lineages. Autologous HSCs therefore make the transplant procedure available to all patients, avoid the immunological compatibility problems leading to GvHD and allow minimally immunosuppressive conditioning regimens thus drastically reducing infectious complications.

Lentiviral-based HSC gene therapy trials have demonstrated their therapeutic potential in curing genetic diseases. However, difficulties remain with the methods employed for the genetic modification of HSCs.

Current HSC gene therapy protocols (e.g. Cartier N et al. Science 2009; 326:818-823; Cavazzana-Calvo M et al. Nature 2010; 467:318-322; Biffi A et al. Science 2013; 341:1233158; Aiuti A et al. Science. 2013; 341:1233151) use a 2-4 day ex vivo culture during the HSC genetic modification process. Longer culture times typically yield higher transduction levels. However, ex vivo culture negatively impacts on HSC function and this negative effect clearly correlates with the duration of culture (Guenechea G et al. Blood 1999; 93:1097-1105; Xu R et al. Transfusion 2001; 41:213-218; Mazurier F et al. Blood 2004; 103:545-552; Ahmed et al. Blood 2004; 103:2079-2087; Glimm H et al. Exp. Hematol. 2005; 33:20-25; Kallinikou K et al. Br. J. Haematol. 2012; 158:778-787). Although some progress has been made towards improving the ex vivo expansion of HSCs (Zhang C C et al. Blood 2008; 111:3415-3423; Boitano A E et al. Science 2010; 329:1345-1348; Delaney C et al. Nat. Med. 2010; 16:232-236; Himburg H A et al. Nat. Med. 2010; 16:475-482; Csaszar E et al. Cell Stem Cell 2012; 10:218-229; Walasek M A et al. Ann. N. Y. Acad. Sci. 2012; 1266:138-150), the resulting protocols present several challenges for clinical translation, give variable and often poorly reproducible results, and still need to be proven in relevant clinical settings. Consequently ex vivo culture in the context of HSC gene therapy should be kept as short as possible.

Accordingly, there is a need for devising improved protocols that allow efficient genetic modification of haematopoietic stem cells while minimising culture time. Furthermore, the improved protocols need to be suitable for clinical use.

SUMMARY OF THE INVENTION

We have unexpectedly shown that $CD34^+CD38^-$ HSCs undergo more efficient transduction when they are present at high purity. We have developed a protocol for purifying and transducing these cells in a manner that is suitable for clinical use.

We have also found that prostaglandin E2 and derivatives thereof increase the efficiency of gene transfer into $CD34^+$ and $CD34^+CD38^-$ HSCs.

These unexpected findings result in increased transduction efficiency which allows reduction in the quantity of vector applied and minimisation of ex vivo culture.

Continuing from these findings, we have developed an innovative protocol which is based on the co-transplantation of transduced, highly-purified long-term repopulating cells (e.g. cells expressing CD34, but not CD38) with unmanipulated progenitor cells (e.g. cells that express CD38). This protocol may improve safety and efficacy of gene therapy by:
1. increasing transduction efficiency;
2. reducing the number of cells necessary to be transduced, which results in a lower integration load required to be infused into the subject;
3. guaranteeing a rapid hematologic recovery.

In addition, we have also developed an innovative protocol which is based on the transplantation of transduced haematopoietic progenitor cells.

According to a first aspect of the present invention there is provided a method of preparing a therapeutic cell population for clinical use from a starting population of cells comprising haematopoietic stem cells, said method comprising separating a population of cells that substantially do not express CD38 but which express CD34 from the starting population of cells, and transducing the separated cell population with a vector, preferably a viral vector, to obtain the therapeutic cell population.

In one embodiment of the present invention the method comprises the steps of:
 a. separating CD38-expressing cells from a starting population of cells comprising haematopoietic stem cells;
 b. separating CD34-expressing cells from the population of cells obtained in step (a) that do not express CD38;
 c. transducing the CD34-expressing cell population obtained in step (b) with a vector to obtain the therapeutic cell population.

In another embodiment the method comprises the steps of:
 a. contacting a starting population of cells comprising haematopoietic stem cells with an agent reactive for CD38;
 b. separating the CD38-reactive cells from the CD38-non-reactive cells;
 c. contacting the CD38-non-reactive cells obtained in step (b) with an agent reactive for CD34;
 d. separating the CD34-reactive cells from the CD34-non-reactive cells wherein the CD34-reactive cells form the transduction cell population;
 e. transducing the transduction cell population with a vector to obtain the therapeutic cell population.

The therapeutic cell population may have the $CD34^+CD38^-$ phenotype.

In one embodiment the vector comprises a nucleotide of interest or is itself a nucleotide of interest.

In one embodiment the separated CD38-expressing cells or CD38-reactive cells or portion thereof are retained to form a support cell population. The support cell population may have the $CD34^+CD38^{int1}$, $CD34^+CD38^{int2}$ and/or $CD34^+CD38^+$ phenotype.

In one embodiment of the present invention the step of transducing a population of cells with a vector comprises culturing the cells for about 44 h or more. The "step of transducing a population of cells with a vector" is to be understood as the pre-stimulation and vector exposure phases. For example, the population of cells may be cultured for about 44-66 h, 44-60 h, 44-54 h or 44-48 h during the step of transduction with a vector. In one embodiment the population of cells is cultured for about 66, 60, 54, 48 or 44 h during the step of transduction with a vector.

In another embodiment of the present invention the step of transducing a population of cells with a vector comprises culturing the cells (i.e. during pre-stimulation and vector contact) for less than about 44 h. For example, the population of cells may be cultured for about 12-42 h, 12-36 h, 12-24 h or 12-18 h during the step of transduction with a vector. In one embodiment the population of cells is cultured for about 42, 36, 30, 24, 18 or 12 h during the step of transduction with a vector. Preferably the population of cells is cultured for about 24 h during the step of transduction with a vector.

In one embodiment of the present invention prostaglandin E2 or a derivative thereof is used in the methods of the invention to increase the transduction efficiency.

Prostaglandin E2 or a prostaglandin E2 derivative (e.g. 16,16-dimethyl prostaglandin E2 (dmPGE2)) may be added to the population of cells during the step of transduction with a vector, preferably during the pre-stimulation phase of this step. Prostaglandin E2 or the prostaglandin E2 derivative may be added at the start of the pre-stimulation phase, or during the pre-stimulation phase. For example, prostaglandin E2 or the prostaglandin E2 derivative may be added about 1, 2, 3, 4, 5, 6, 7, 8, 9, 10, 11 or 12 h before the exposure of the population of cells to the vector. Preferably, the prostaglandin E2 or the prostaglandin E2 derivative is added to the population of cells during the pre-stimulation phase, about 2 h before the exposure of the cells to the vector. In another embodiment the prostaglandin E2 or the prostaglandin E2 derivative is added to the population of cells at the same time as exposure to the vector.

In one embodiment of the present invention the starting population of cells comprising haematopoietic stem cells is obtained from a tissue sample.

In another embodiment the starting population of cells comprising haematopoietic stem cells is obtained from mobilised peripheral blood, bone marrow or umbilical cord blood.

In another aspect, the present invention provides a therapeutic cell population prepared according to a method of the invention.

In another aspect, the present invention provides a support cell population prepared according to a method of the invention.

In another aspect, the present invention provides a pharmaceutical composition comprising the therapeutic cell population or support cell population of the invention, preferably in the presence of a pharmaceutically acceptable carrier, diluent or excipient.

In another aspect, the present invention provides a therapeutic cell population and/or a support cell population for use in medicine.

In one embodiment the therapeutic cell population is administered in combination with the support cell population of the invention.

In another embodiment the therapeutic cell population is administered to a subject prior to administration of the support cell population.

In another embodiment the therapeutic cell population is administered to a subject contemporaneously with or simultaneously to administration of the support cell population.

In another aspect, the present invention provides a kit comprising the therapeutic and support cell populations of the invention.

In another aspect, the present invention provides a method of treatment comprising administering the therapeutic cell population of the invention to a subject in need thereof.

In another aspect, the present invention provides a method of treatment comprising administering the therapeutic cell population of the invention and the support cell population of the invention to a subject in need thereof.

Preferably, the treatment is a treatment by gene therapy.

In another aspect, the present invention provides a haematopoietic progenitor cell population for use in gene therapy, wherein the haematopoietic progenitor cell population has been transduced with a nucleotide of interest.

The step of transduction with a nucleotide of interest may, for example, utilise any of the methods of cell transduction described herein.

In another aspect, the present invention provides a haematopoietic progenitor cell population for use in gene therapy, wherein said cells have been separated from a population of cells comprising haematopoietic stem and progenitor cells and then transduced with a nucleotide of interest.

In one embodiment the haematopoietic progenitor cell population has the $CD34^+CD38^{int}$ phenotype. In another embodiment, the haematopoietic progenitor cell population has a $CD34^+CD38^{int1}$, $CD34^+CD38^{int2}$ and/or $CD34^+CD38^+$ phenotype. Thus the haematopoietic progenitor cell population may, for example, not comprise cells of the $CD34^+CD38^-$ phenotype.

In another embodiment the transduced progenitor cell population is administered in combination with a population of haematopoietic stem cells, for example a population of cells with the $CD34^+CD38^-$ phenotype.

In another aspect, the present invention provides a method of gene therapy comprising administering a haematopoietic progenitor cell population to a subject in need thereof, wherein the haematopoietic progenitor cell population has been transduced with a nucleotide of interest.

In another aspect, the present invention provides a method of controlling the duration of transgene expression in a patient, wherein the duration of transgene expression is controlled by selectively administering transduced haematopoietic stem and/or progenitor cells based on CD38 expression level. Increased transgene expression duration may be achieved by administering cells with decreased levels of CD38 expression.

In another aspect, the present invention provides the use of prostaglandin E2 or a prostaglandin E2 derivative for increasing gene transfer efficiency when transducing haematopoietic stem or progenitor cells with a vector, preferably a viral vector.

In one embodiment the prostaglandin E2 derivative is 16,16-dimethyl prostaglandin E2.

Prostaglandin E2 or a prostaglandin E2 derivative (e.g. 16,16-dimethyl prostaglandin E2 (dmPGE2)) may be added to the population of cells during the pre-stimulation phase. In one embodiment the prostaglandin E2 or the prostaglandin E2 derivative is added at the start of the pre-stimulation phase. In another embodiment the prostaglandin E2 or the prostaglandin E2 derivative is added during the pre-stimulation phase.

For example, prostaglandin E2 or the prostaglandin E2 derivative may be added about 1, 2, 3, 4, 5, 6, 7, 8, 9, 10, 11 or 12 h before the exposure of the population of cells to the vector. Preferably, the prostaglandin E2 or the prostaglandin E2 derivative is added to the population of cells during the pre-stimulation phase, about 2 h before the exposure of the cells to the vector.

In another embodiment the prostaglandin E2 or the prostaglandin E2 derivative is added to the population of cells at the same time as exposure to the vector.

In another aspect, the present invention provides a method of transducing a population of cells with a vector, preferably a lentiviral vector, wherein the step of transducing a population of cells with a vector comprises culturing the cells for about 44 h or more. The "step of transducing a population of cells with a vector" is to be understood as the pre-stimulation and vector exposure phases. For example, the population of cells may be cultured for about 44-66 h, 44-60 h, 44-54 h or 44-48 h during the step of transduction with a vector. In one embodiment the population of cells is cultured for about 66, 60, 54, 48 or 44 h during the step of transduction with a vector.

In another aspect, the present invention provides a method of transducing a population of cells with a vector, preferably a lentiviral vector, wherein the step of transducing a population of cells with a vector comprises culturing the cells (i.e. during pre-stimulation and vector contact) for less than about 44 h. For example, the population of cells may be cultured for about 12-42 h, 12-36 h, 12-24 h or 12-18 h during the step of transduction with a vector. In one embodiment the population of cells is cultured for about 42, 36, 30, 24, 18 or 12 h during the step of transduction with a vector. Preferably the population of cells is cultured for about 24 h during the step of transduction with a vector.

It will be appreciated that the steps of the method of preparing the therapeutic cell population described herein may be carried out in a different order. Thus, the method of preparing the therapeutic cell population may comprise the steps of:

a. separating CD34-expressing cells from a starting population of cells comprising haematopoietic stem cells;
b. separating CD38-expressing cells from the population of cells obtained in step (a) that express CD34;
c. transducing the cell population that does not express CD38 obtained in step (b) with a vector to obtain the therapeutic cell population.

The cells or portion thereof obtained in step (b) that do express CD38 may be retained to form a support cell population.

The present application refers to uses of a support cell population. In one aspect of the present invention, the support cell population referred to herein may be replaced with the support cell population as defined above.

Alternatively, the cells or portion thereof obtained in step (b) that do express CD38 may be transduced with a vector. Such transduced cells could be used in therapy (e.g. administered to a subject). This approach may allow transient delivery of a gene (e.g. a therapeutic gene) to a subject (such as for use in cancer gene therapy).

Figure 1A:
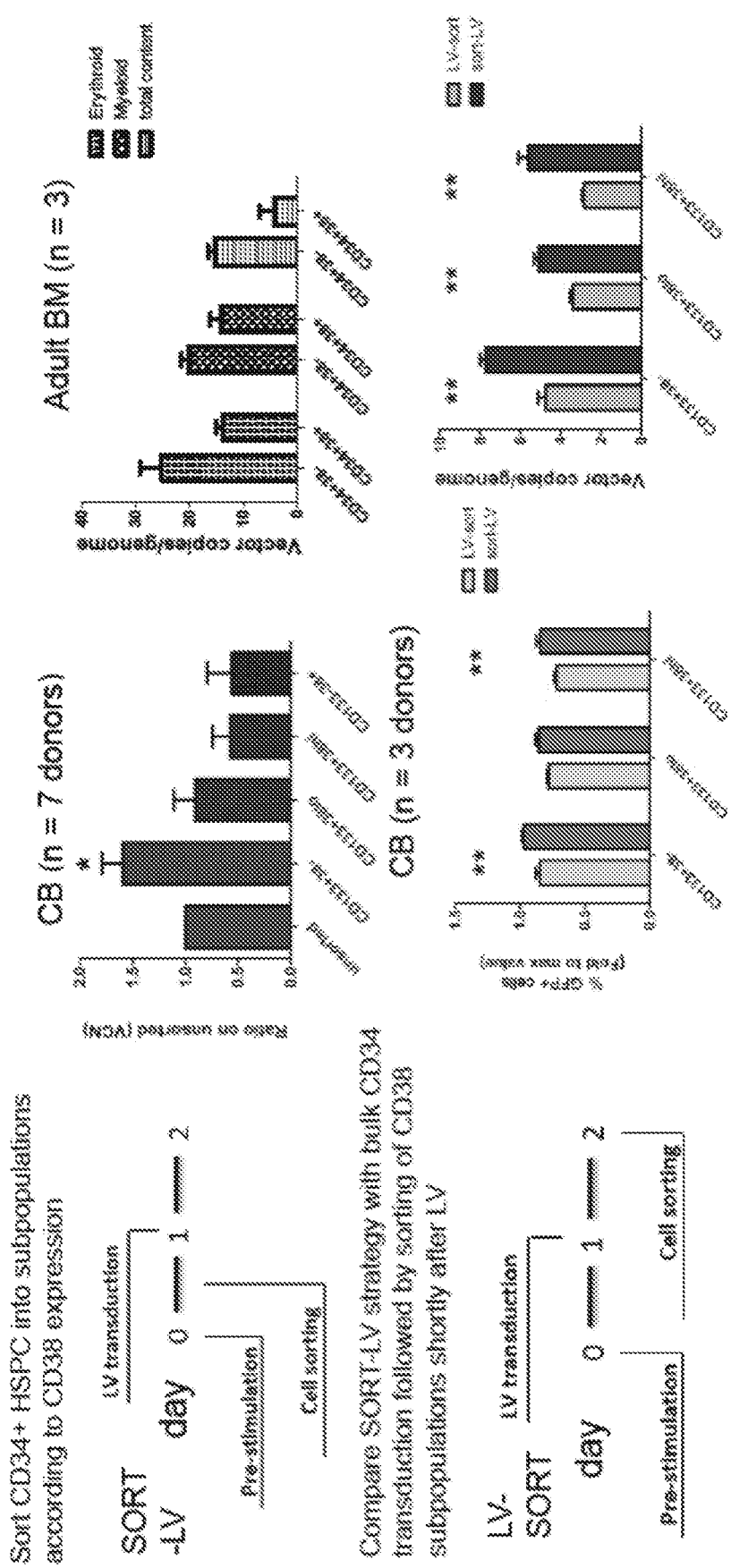
FIG. 1
Figure 1C:
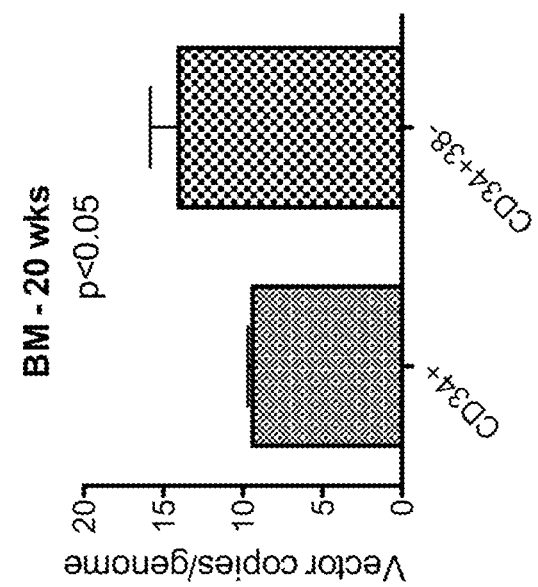

(A) $CD34^+$ cells from cord blood or adult bone marrow (Lonza) were thawed, pre-stimulated with SCF, FLT3L, TPO and IL6 for 12 h, stained with anti-CD34, anti-CD133 and anti-CD38 antibodies and FACS-sorted into the subpopulations indicated on the x-axis of the bar graphs. The SORT-LV protocol encompasses transduction with a lentiviral vector (PGK.GFP, $10^8$ TU/mL) 12 h after sorting, while in the LV-SORT protocol bulk $CD34^+$ cells are lentiviral vector-transduced after 24 h of pre-stimulation, followed by sorting the day after. Transduction efficiencies were measured by vector copy number (VCN) analysis after 14 d of in vitro culture in differentiating conditions (colony forming assay or liquid culture) or by flow cytometric analysis after 7 d of culture (green bar graph, bottom left panel). In the case of bone marrow, VCN was determined both on the total colony outgrowth, or on myeloid and erythroid colonies separately by plucking single colonies under microscopic guidance.

(B) $CD34^+$ cells from 4 cord blood donors (Lonza) were thawed and divided in 2 groups: Bulk: $CD34^+$ cells; Stem: sorted $CD34^+CD38^-$ cells obtained from bulk (CD38 gate: lowest 10%; CD38 antibody: IB2-PEVio770, Miltenyi). Both groups were placed in culture at a density of $10^6$ cells/mL in Stem span serum free medium (SFEM) supplemented with 100 ng/mL SCF, 100 ng/mL FLT3L, 50 ng/mL TPO, 50 ng/mL IL-6 and pre-stimulated for 18 h. Transduction was performed with a PGK.GFP lentiviral vector at $10^8$ TU/mL. Cells were injected into sublethally irradiated, 8 week old NSG mice (Bulk: $1.26 \times 10^5$ cells/mouse; n=6; Stem: $1.8 \times 10^4$ cells/mouse; n=6). Vector copy number was assessed by qPCR performed on peripheral blood nucleated cells at 3 months post transplantation, using primers specific for human cells.

(C) VCN performed at 20 weeks post transplantation on BM from the hematochimeric mice described in (B). The higher level of gene transfer into CD34$^+$CD38$^-$ cells with respect to total CD34$^+$ cells is maintained long-term in the xenografts deriving from the respective starting populations.

FIG. 2

Total Cord Blood (40 mL) was collected from the umbilical vein after C-section delivery, according to approved protocols at Ospedale san Raffaele.

Mononuclear cells ($2 \times 10^8$) were isolated by Ficoll, and marked with a cocktail of lineage antibodies and CD38 (Miltenyi, Cat 130-092-263). Positively labelled cells ($10^8$) were linked to magnetic microbeads and separated by an LD column (Miltenyi).

The flow-through ($10^8$ Lin$^-$/CD38$^-$ cells) was incubated with CD34 microbeads (Miltenyi), and CD34$^+$CD38$^-$ cells were enriched on an MS column.

To allow tracking of the haematopoietic output of CD38$^+$ and CD38$^-$ subpopulations in NSG mice, the Lin$^+$/CD38$^+$ (first column) and the CD34$^+$CD38$^-$ fractions (second column) were FACS-sorted for CD34 (yielding highly pure CD34$^+$CD38$^+$ and CD34$^+$CD38$^-$ cells, respectively)

Reanalysis shows efficient, bead-based separation into CD38$^{-/low}$ and CD38$^+$ cells. These fractions were then differentially marked with a GFP- and an OFP-expressing lentiviral vector, mixed in a 1:5 ratio (CD34$^+$38$^-$:CD34$^+$38$^+$) and injected into n=4 NSG mice. GFP/OFP chimerism was followed for 28 weeks.

FIG. 3

Modelling stem/progenitor co-transplantation in NSG mice: bone marrow CD38$^-$ versus CD38$^{high}$.

CD34$^+$ adult bone marrow haematopoietic stem and progenitor cells (HSPCs) were sorted into CD34$^+$CD38$^-$ (+/−) and CD34$^+$CD38$^{hi}$ (+/hi) cells, pre-stimulated in Stem Span SFEM containing SCF (300 ng/mL), Flt3L (300 ng/mL), TPO (100 ng/mL), IL6 (60 ng/mL) and dmPGE2 (10 μM) for 16 h and transduced with a GFP-LV (+/−) or OFP-LV (+/hi). After 24 h of transduction, cells were injected into 8 week old, sublethally irradiated NSG mice as follows:

Group 1: 27,000 CD34$^+$CD38$^-$ cells per mouse (n=3);
Group 2: 248,000 CD34$^+$CD38$^{hi}$ cells per mouse (n=3);
Group 3: 27,000 CD34$^+$CD38$^-$ and 248,000 CD34$^+$CD38$^{hi}$ cells per mouse (n=3)

Engraftment (group 1, 2, 3) and chimerism (group 3) were monitored over time in the peripheral blood, and hematopoietic organs were analysed 18 weeks after transplantation.

FIG. 4

(A) Modelling stem/progenitor co-transplantation in NSG mice: mobilised peripheral blood CD38$^-$ vs. CD38$^{intm1}$ vs. CD38$^{intm2}$ vs. CD38$^{hi}$.

We sorted CD34$^+$ MPB into 4 subsets with increasing levels of CD38 expression (CD34$^+$/CD38$^-$; CD34$^+$/CD38$^{int1}$; CD34$^+$/CD38$^{int2}$; CD34$^+$/CD38$^{hi}$), pre-stimulated these subsets in Stem Span SFEM containing SCF (300 ng/mL), Flt3L (300 ng/mL), TPO (100 ng/mL), IL6 (60 ng/mL) and dmPGE2 (10 μM) for 16 h and transduced the subsets with the following lentiviral vectors: CD34$^+$/CD38$^-$: GreenFP.LV; CD34$^+$/CD38$^{int1}$: CherryFP.LV; CD34$^+$/CD38$^{int2}$: CyanFP.LV; CD34$^+$/CD38$^{hi}$ OrangeFP.LV. After 24 h of transduction, cells were injected into 8 week old, sublethally irradiated NSG mice as follows:

Group 1: 129,000 CD34$^+$/CD38$^-$ cells per mouse (n=6);
Group 2: 869,000 progenitor cells (sum of CD34$^+$/CD38$^{int1}$, CD34$^+$/CD38$^{int2}$ and CD34$^+$/CD38$^{hi}$ cells, each population contributing 33% to the progenitor mix) per mouse (n=7);
Group 3: a mix of 129,000 CD34$^+$/CD38$^-$ and 869,000 pooled progenitor cells per mouse (n=6)

Engraftment (group 1, 2, 3) and chimerism (group 3) were monitored over time in the peripheral blood.

Figure 4A:
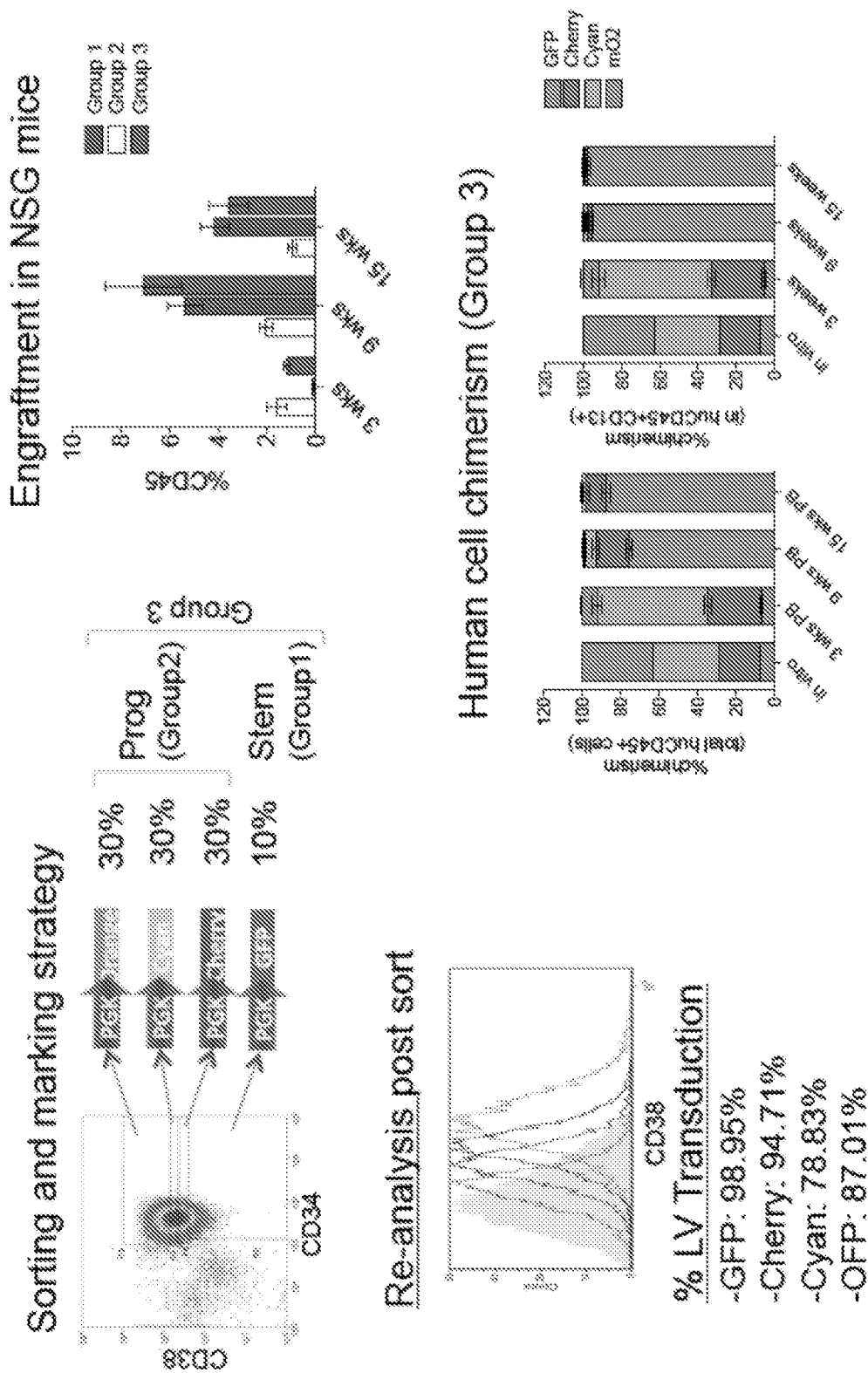

(B) G-CSF-mobilised peripheral blood CD34$^+$ cells were sorted according to CD38 expression levels and diverse fractions were marked by 4 lentiviral vectors expressing different fluorescence proteins, as described in FIG. 4(A) above. Differentially marked fractions were pooled (corresponding to Group 3 in FIG. 4(A)) and injected into 8 week old sublethally irradiated NSG mice. N=2 mobilised peripheral blood donors (CD34$^+$ cells bought from Stem Cell Technologies), 2 independent experiments.

The relative contribution from the CD38 subfractions to the human graft over time is shown (n=10 mice per timepoint, 6 from Experiment 1 and 4 from Experiment 2; mean+/−sem).

Experiment 1:
Group 3, a mix of 129,000 CD34$^+$CD38$^-$ (0-12%) and 869,000 CD34$^+$CD38$^{low-intm-high}$ (12-100%) pooled progenitors cells per mouse (n=6).

Experiment 2:
Group 3, a mix of 149,000 CD34$^+$CD38$^-$ (0-12%) and 1,320,000 CD34$^+$CD38$^{low-intm-high}$ (12-100%) pooled progenitor cells per mouse (n=4).

FIG. 5

(A) The effect of dmPGE2 on cord blood CD34$^+$ cells (in vitro).

CD34$^+$ cells from n=4 cord blood donors (Lonza) were thawed and put into culture in Stem span serum free expansion medium (SFEM) supplemented with 100 ng/mL SCF, 100 ng/mL FLT3L, 50 ng/mL TPO, 50 ng/mL IL6 for 18 h (pre-stimulation), in the presence or absence of 10 μM dmPGE2. After pre-stimulation, cells were incubated with $10^8$ TU/mL of a lentiviral vector for 24 h. Cells were then cultured in vitro (n=5 replicates) for 14 days in IMDM+10% FCS before vector copy number (VCN) was measured by qPCR as described in Gentner, B. et al. (2009) *Nat. Methods* 6: 63-6. dmPGE2 pre-stimulation resulted in a 50% increase in gene transfer.

(B) The effect of dmPGE2 on G-CSF-mobilised CD34+ peripheral blood stem cells (in vitro).

N=6 transductions of 3 mobilised peripheral blood donors. Cells were thawed, resuspended in serum-free, commercial culture medium (e.g. CellGro) at a density of $10^6$ cells/mL in the presence of the following cytokines: 300 ng/mL SCF, 300 ng/mL FLT3L, 100 ng/mL TPO, 60 ng/mL IL-3, and prestimulated for 18 h, in the absence (control, Ctrl) or presence of dmPGE2. Transduction was performed with lentiviral vectors (3 different batches) at $10^8$ TU/mL for 12-24 h. Vector copy number was assessed by qPCR after 14 days of in vitro culture in IMDM and 10% FCS. Relative VCN (normalised to the Control group) is shown.

(C) The effect of the timing of dmPGE2 stimulation on the transducability of human HSPCs by lentiviral vectors.

The effect seems to be maximised when dmPGE2 is added 2 h before LV exposure (t=−2 h: 100% increase in VCN), while adding dmPGE2 at the time of thawing (t=−16 h) resulted in a ~50% VCN increase, similar to the experiments shown in (A) and (B). This experiment was carried out on 1 cord blood and 1 mobilised peripheral blood donor, the relative VCN is shown (normalised to its respective control).

(D) The increased vector copy number obtained by dmPGE2 stimulation ex vivo is maintained long-term in the progeny of cord blood-derived CD34$^+$ cells after xenotransplantation.

Cord blood CD34$^+$ cells were thawed and placed in culture (10$^6$ cells/mL) in Stem span serum free medium (SFEM) supplemented with 100 ng/mL SCF, 100 ng/mL FLT3L, 50 ng/mL TPO, 50 ng/mL IL-6 for 18 h (pre-stimulation) and subsequently transduced with a lentiviral vector at 10$^8$ TU/mL for 24 h. Cells were injected into sublethally irradiated, 8 week old NSG mice (1.5-3×10$^5$ cells per mouse), and vector copy number (VCN) was analysed in the pooled blood or bone marrow of each group of mice at the indicated time-points using primers specific for human cells. 3 replicate experiments are shown. Left graph: Cells were transduced with a PGK.TRAIL LV, and 10 µM dmPGE2 (dmPGE2 group, n=5 mice) or DMSO (Ctrl group, n=5 mice) was added directly after thawing (t=−16 h with respect to vector addition). Middle graph: Cells were transduced with a PGK.TRAIL LV, and 10 µM dmPGE2 (dmPGE2 group n=5) or DMSO (Ctrl group; n=8) was added 120 min before vector addition (t=−2 h). Middle graph: Cells were transduced with a PGK.OFP LV, and 10 µM dmPGE2 (dmPGE2 group n=5) or DMSO (Ctrl group; n=5) was added 120 min before vector addition (t=−2 h). In all three experiments, the benefit in transduction observed in vitro was stably maintained long-term, up to 18 weeks after xenotransplantation.

(E-G) The increased vector copy number obtained by dmPGE2 stimulation ex vivo is maintained long-term in the progeny of CD34$^+$ cells from adult sources (such as mobilised peripheral blood) only when specific culture conditions are used, namely reducing total culture time to less than 44 h.

CD34$^+$ cells from G-CSF mobilised peripheral blood (mPB) were thawed and placed in culture (10$^6$ cells/mL) in CellGro medium supplemented with SCF (300 ng/mL), FLT3L (300 ng/mL), TPO (100 ng/mL) and IL-3 (60 ng/mL). Cells were transduced with third generation lentiviral vectors coding for gp91$^{phox}$ (vectors suitable for the gene therapy of chronic granulomatous disease) at a dose of 10$^8$ TU/mL. The different protocols used for ex vivo transduction of mPB CD34+ cells are illustrated in (E) and differ in terms of the presence (P1, P2, P3) or absence (P0, P4) of dmPGE2, the timing of dmPGE2 addition (after thawing: P1, P2; 120 min before transduction: P3) and the duration of culture (24 h: P2, P4 versus 44 h: P0, P1, P3).

(F) 10×10$^6$ CD34$^+$ mPB cells from donor 1 were thawed, divided into 4 equal parts and transduced with the SP146/gp91.cogp91$^{phox}$.126T LV from an industry-grade production (Molmed Spa) according to P0, P1, P2 or P3. The outgrowth of 5×10$^5$ cells put into culture at time zero was injected per mouse (actual numbers: P0 3.66×10^5 per mouse; P1: 4.66×10^5 per mouse; P2: 3.0×10^5 per mouse; P3: 4.86×10^5 per mouse). Mice were euthanised at 20 weeks post transplantation. BM was flushed and pooled from the mice belonging to the same group (P0, P1, P2: n=5 per group; P3: n=3 per group) and depleted for mouse cells. Enriched human cells were then subjected to vector copy number (VCN) analysis using primers specific for human cells (5 technical replicates). Statistics were performed by One-way ANOVA with Bonferroni post-test correction, and demonstrate a ~50% increase in VCN into long-term repopulating cells in the P2 condition.

Figures 5A, 5B, 5C, 5D:
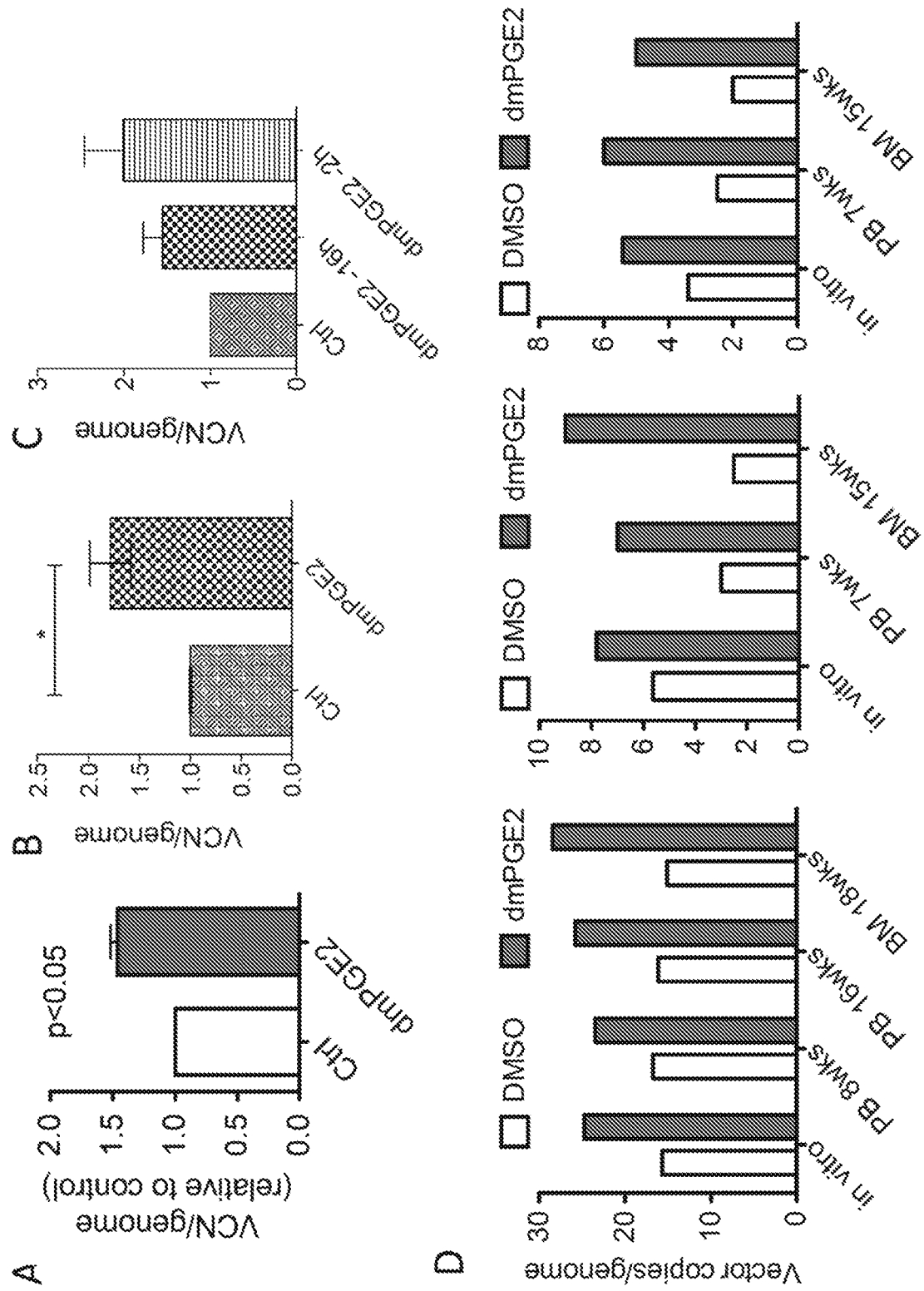

A replicate experiment was performed using mPB CD34$^+$ cells from a second donor (G). 15×10$^6$ CD34$^+$ mPB cells were thawed, divided into 4 equal parts and transduced with the SP146/gp91.gp91$^{phox}$TGT.126T LV (a vector suitable for CGD gene therapy) coming from a lab-grade production according to protocols P0, P1 (44 h−/+dmPGE2) or P4, P2 (24 h−/+dmPGE2). The outgrowth of 9×10$^5$ cells put into culture at time zero was injected per mouse (actual numbers: P0 10×10$^5$ per mouse; P1: 8.2×10$^5$ per mouse; P4: 4.5×10$^5$ per mouse; P2: 5.3×10$^5$ per mouse). VCN was analysed on BM cells from each single mouse 13 weeks after transplantation using a qPCR assay specific for human cells. In line with the first experiment, the P1 condition did not result in a sustained gain in transduction efficiency mediated by dmPGE2 in long-term repopulating cells from adult sources, in stark contrast to MPB CD34$^+$ progenitor cells where the P1 protocol has resulted in increased VCN using in vitro readouts (see FIG. 5B), and in contrast to cord blood where dmPGE2 associated to the "standard" culture protocol leads to increased VCN in long-term repopulating cells (FIG. 5D). Unexpectedly, we found that shortening the MPB CD34$^+$ cell culture protocol to 24 h (P2) not only rescued the transduction-promoting effect of dmPGE2 in long-term repopulating cells but also increased transduction well above levels achieved by a 44 h standard protocol. Possible explanations include

- an exposure time-dependent effect of dmPGE2 on HSC (but not on progenitors) where the window of permissiveness to LV transduction is limited to 16-24 h (in line with this hypothesis: even though not statistically significant, the P3 protocol in which dmPGE2 exposure was postponed with respect to P1 may suggest some increase in VCN; see FIG. 5F)
- the existence of functionally different HSC species, one that is sensitive to dmPGE$_2$ stimulation but loses engraftment potential after 24 h in culture, and one that is insensitive to dmPGE2 but better maintains engraftment potential in culture thus predominating in longer cultures

FIG. 6

The use of dmPGE2 increases gene transfer into CD34$^+$, CD34$^+$CD38$^-$ HSC and CD34$^+$CD38$^+$ progenitor cells from adult bone marrow.

The experiments were carried out as follows: CD34$^+$ cells from N=3 bone marrow donors (Lonza) were thawed and put into culture in Stem span serum free expansion medium (SFEM) under the following conditions: pre-stimulation in 300 ng/mL SCF, 300 ng/mL FLT3L, 100 ng/mL TPO, 60 ng/mL IL3 for 18 h. Cells were then divided into 3 groups: bulk CD34$^+$, CD34$^+$CD38$^-$, CD34$^+$CD38$^+$ (FACS-sorted on a MoFlow cytometer after marking with CD38-APC antibody from BD Bioscience). We then added dmPGE2 (10 µM) or DMSO to the cultures, and pre-stimulated the cells for another 16 h before they were transduced with a GFP-expressing lentiviral vector (LV.PGK.GFP) at 10$^8$ TU/mL. In vitro culture assays were performed, either as liquid culture for 14 days in IMDM+10% FCS (left) or colony forming cell (CFC) assay (right; plated 800 cells/mL methocult, analysed colony outgrowth after 14 d). Vector copy number was assessed by qPCR as described in Gentner B et al. Nat. Methods 2009; 6:63-66.

FIG. 7

Modelling the co-administration of cultured/transduced CD34$^+$CD38$^-$ stem cells with uncultured CD34$^+$CD38$^{int/+}$ progenitor cells.

G-CSF-mobilised peripheral blood cells were obtained by leukapheresis, enriched for CD34$^+$ cells, sorted into a more primitive CD38⁻ stem cell fraction (0-7% CD38 percentile) and a CD38$^{int/+}$ progenitor cell fraction (13-100% CD38 percentile) by FACS (MoFlo XDP sorter and CD38 PE-Vio770 Miltenyi antibody). Multiple aliquots of each fraction were frozen.

Figure 7A:
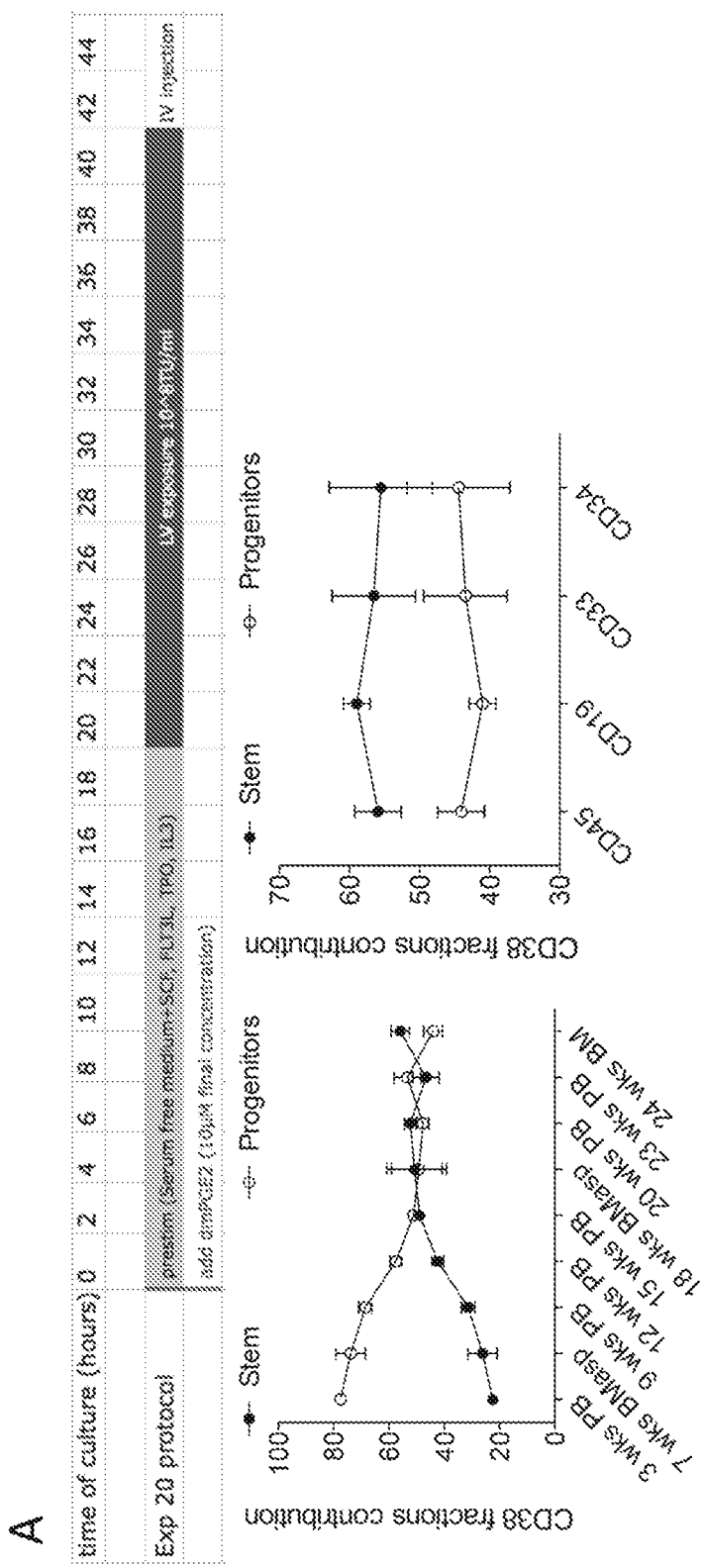

(A) The CD34⁺CD38⁻ (Stem) fraction was thawed, resuspended in Stem Span serum free expansion medium (SFEM) supplemented with 300 ng/mL SCF, 300 ng/mL FLT3L, 100 ng/mL TPO, 60 ng/mL IL-3 and 10 μM dmPGE2 at a density of $10^6$ cells/mL. Cells were pre-stimulated for 20 h (grey box in the scheme) and transduced with a PGK.GFP lentiviral vector ($10^8$ TU/mL) for 24 h (red box) as shown in the scheme. Cultured/gene-modified stem cells were then mixed with freshly thawed CD34⁺CD38$^{int/+}$ progenitors in a 1:8 ratio, and injected into 8 week old, sublethally irradiated NSG mice (47,400 CD34⁺CD38⁻/327,000 uncultured progenitor cells per mouse, n=6). Transduction efficiency of the stem compartment was 95% in vivo, as measured in NSG mice exclusively transplanted with CD34⁺CD38⁻ stem cells (n=6). The left-hand graph shows the percentage of GFP+ cells in the human graft (closed circles) at the indicated time-points as a surrogate marker for cells deriving from cultured CD34⁺CD38⁻ cells, and the percentage of GFP-cells (open circles) as a surrogate marker for cells deriving from the uncultured progenitor cell graft. At 24 weeks post-BMT, a time-point reflective of HSC-derived haematopoiesis, around 60% of the graft were GFP+ and thus derived from the CD34⁺CD38⁻ stem cell fraction. This figure was similar for all lineages (right-hand graph) including B cells (CD19⁺), myeloid cells (CD33⁺) and CD34⁺ HSPC. On the other hand, 30-40% of the long-term graft seems to be derived from CD34⁺CD38$^{int/+}$ progenitors, a fraction that was unexpectedly high as compared to the studies described in FIG. 4. Moreover, it took 15 weeks before equilibrium between stem and progenitor cell contribution was reached (FIG. 7A), as opposed to 9 weeks in the studies described in FIG. 4B.

(B) In order to improve the gene therapy protocol based on infusion of highly enriched gene-modified HSC and uncultured progenitor cell support, we modulated the ratio of stem to progenitor cells (1:5 vs. 1:10) and the culture conditions (reduced culture time to 24 h, avoiding progenitor cell cytokines such as IL3) to allow better maintenance of HSC functions in the CD34⁺CD38⁻ cells. CD34⁺CD38⁻ (Stem) cells from the same donor as in (A) were thawed, resuspended in CellGro medium supplemented with 300 ng/mL SCF, 300 ng/mL FLT3L, 100 ng/mL TPO and 10 μM dmPGE2 at $10^6$/mL and pre-stimulated for 16 h (grey box in the scheme). Transduction was performed with a PGK.GFP lentiviral vector at $10^8$ TU/mL for 8 h (red box) as showed in the scheme. Cultured/gene-modified stem cells were then mixed with freshly thawed CD34⁺CD38$^{int/+}$ progenitors in a 1:5 (46,500 CD34⁺CD38⁻/232,500 uncultured progenitor cells per mouse, n=5) or 1:10 (46,500 CD34⁺CD38⁻/465,000 uncultured progenitor cells per mouse, n=5) ratio and injected into 8 week old, sublethally irradiated NSG mice. The upper graphs show the percentage of GFP+ cells in the human graft (closed circles) at the indicated time-points as a surrogate marker for cells deriving from cultured CD34⁺CD38⁻ cells, and the percentage of GFP-cells (open circles) as a surrogate marker for cells deriving from the uncultured progenitor cell graft. A much faster contribution from the transduced CD34+CD38-stem cells was noted, reaching up to 70% already at 12 weeks (compared to 40% in FIG. 7A). The fraction of GFP+ cells was similar in short-lived hematopoietic lineages (CD33⁺ or CD34⁺ cells) irrespectively from the stem/progenitor ratio of 1:5 or 1:10 (bottom graphs). These data support the notion that a short culture time is critical for obtaining highly functional, gene-modified HSC

FIG. 8

Tailoring the persistence of gene-modified cells during gene therapy.

(A) Stable long term transgene expression is achieved by administering transduced CD34⁺CD38⁻ cells with untransduced CD34⁺CD38$^{+/int}$ progenitor cells. Such an approach may be well suited to treating inherited genetic disorders.

(B) Transient short term transgene expression is achieved by administering transduced CD34⁺CD38$^{+/int}$ progenitor cells with untransduced CD34⁺CD38⁻ cells.

(C) Transient medium term expression is achieved by administering transduced CD34⁺CD38$^{int/lo}$ cells with untransduced CD34⁺CD38⁻ cells.

The approaches shown in (B) and (C) may be well suited to targeting tumours.

These figures show data from 2 independent experiments (donor 1: n=21 mice; donor 2: n=12 mice).

FIG. 9

Impact of ex vivo culture time on the engraftment of HSPC fractions (B and C: total CD34⁺ HSPC; D: CD34⁺CD38⁻ HSPC; E: CD34⁺CD38$^{int/+}$ progenitor cells)

(A) Scheme of ex vivo culture conditions tested. All experiments were done on G-CSF mobilized peripheral blood (mPB) stem cells collected by leukapheresis. Cells were thawed and placed in culture ($10^6$ cells/mL) in serum-free medium supplemented with 300 ng/mL SCF, 300 ng/mL FLT3L, 100 ng/mL TPO, 60 ng/mL IL-3 for either 24 h (Standard) or 16 h (Short), as indicated in the scheme by grey boxes. Transduction was carried out with third generation lentiviral vectors at $10^8$ TU/mL for 20 h (Standard) or 8 h (Short protocol) as indicated by red boxes (darker boxes). An equivalent number of cells (according to input number at the start of ex vivo culture) were injected into sublethally irradiated, 8 weeks old NSG mice, and engraftment was monitored overtime. Statistics were done by two-way ANOVA with Bonferroni post-test.

(B) (Left) Human CD45⁺ engraftment in the peripheral blood (PB) and bone marrow (BM) of NSG mice at the indicated time point post xenotransplantation with SP146/gp91.cogp91$^{phox}$.126T LV transduced mPB CD34⁺ cells manipulated according to the standard or the short protocol (n=5 mice per group each injected with the outgrowth of $5\times10^5$ mPB CD34⁺ cells). (Right) Engraftment levels were normalised to the actual number of CD34⁺ cells that were injected into each mouse. This number was lower for the short culture protocol since the cells had less time to proliferate in vitro.

(C) A replicate experiment similar to the one described in (B) confirmed that CD34⁺ cells cultured for a shorter duration (24 h versus 44 h) had a significantly increased repopulating potential.

(D) Human CD45⁺GFP+ engraftment in the peripheral blood (PB) and bone marrow aspirate (BMasp) of NSG mice at the indicated time points post xenotransplantation with PGK.GFP LV transduced mPB CD34⁺CD38⁻ stem and early progenitor cells manipulated according to the short (n=6 mice, $4.7\times10^4$ cells per mouse) or the standard protocol (n=6 mice, $4.7\times10^4$ cells per mouse). The level of CD38⁻ was defined as 7% of CD34⁺ cells ranked according to the level of CD38 staining when incubated with an anti-CD38 antibody (IB6-PE-Vio770, Miltenyi) and starting from the lowest CD38 expressing cells (0-7% interval, 0 being the lowest and 100% being the highest expressing cell).

(E) Human CD45+ engraftment in the peripheral blood (PB) and bone marrow aspirate (BMasp) of NSG mice at the indicated time point post xenotransplantation with PGK-.GFP LV transduced mPB CD34+CD38$^{int/+}$ progenitor cells manipulated according to the standard (n=4 mice) or the short protocol (n=5 mice). In addition, n=5 mice were xenotransplanted with freshly thawed (uncultured) CD34+ CD38$^{int/+}$ progenitor cells. Mice were injected with the equivalent of 5×10$^5$ mPB CD34+CD38$^{int/+}$ cells. The level of CD38$^{int/+}$ was defined as 87% of CD34+ cells ranked according to the level of CD38 staining when incubated with an anti-CD38 antibody (IB6-PE-Vio770, Miltenyi) and starting from the highest CD38 expressing cells (13-100% interval, 0 being the lowest and 100% being the highest expressing cell).

FIG. 10

Scheme of potential transduction protocols to be used for clinical gene therapy applications. Protocols A, B, C and D are preferred protocols.

DETAILED DESCRIPTION OF THE INVENTION

Various preferred features and embodiments of the present invention will now be described by way of non-limiting examples.

The practice of the present invention will employ, unless otherwise indicated, conventional techniques of chemistry, molecular biology, microbiology and immunology, which are within the capabilities of a person of ordinary skill in the art. Such techniques are explained in the literature. See, for example, J. Sambrook, E. F. Fritsch, and T. Maniatis (1989) Molecular Cloning: A Laboratory Manual, Second Edition, Books 1-3, Cold Spring Harbor Laboratory Press; Ausubel, F. M. et al. (1995 and periodic supplements) Current Protocols in Molecular Biology, Ch. 9, 13, and 16, John Wiley & Sons, New York, N.Y.; B. Roe, J. Crabtree, and A. Kahn (1996) DNA Isolation and Sequencing: Essential Techniques, John Wiley & Sons; J. M. Polak and James O'D. McGee (1990) In Situ Hybridization: Principles and Practice; Oxford University Press; M. J. Gait (ed.) (1984) Oligonucleotide Synthesis: A Practical Approach, IRL Press; and, D. M. J. Lilley and J. E. Dahlberg (1992) Methods of Enzymology: DNA Structure Part A: Synthesis and Physical Analysis of DNA Methods in Enzymology, Academic Press. Each of these general texts is herein incorporated by reference.

According to a first aspect of the invention there is provided a method of preparing a therapeutic cell population for clinical use wherein said cells express CD34 but substantially do not express CD38. The cells are prepared from a starting population of cells comprising haematopoietic stem cells. The method comprises separating a population of cells that substantially do not express CD38 but which express CD34 from the starting population of cells, and transducing the separated cell population with a vector, preferably a viral vector, to obtain the therapeutic cell population. Preferably the vector comprises a nucleotide of interest.

A therapeutic cell population is to be understood as a population of cells that gives rise to a therapeutic effect when administered to a subject. The therapeutic effect may be to improve or substantially cure a disease or disorder in a subject, or to reduce or substantially prevent the future presentation of a disease or disorder. For example, it may be possible to identify an inherited genetic disorder through genome sequencing and prevent the disorder presenting through the administration of the therapeutic cell population. The therapeutic cell population may comprise a gene that is useful in gene therapy.

By "clinical use" it is to be understood that the therapeutic cell population is prepared in a form that may be administered to an animal subject, preferably a human subject.

Haematopoietic Stem Cells

A stem cell is able to differentiate into many cell types. A cell that is able to differentiate into all cell types is known as totipotent. In mammals, only the zygote and early embryonic cells are totipotent. Stem cells are found in most, if not all, multicellular organisms. They are characterised by the ability to renew themselves through mitotic cell division and differentiate into a diverse range of specialised cell types. The two broad types of mammalian stem cells are embryonic stem cells that are isolated from the inner cell mass of blastocysts, and adult stem cells that are found in adult tissues. In a developing embryo, stem cells can differentiate into all of the specialised embryonic tissues. In adult organisms, stem cells and progenitor cells act as a repair system for the body, replenishing specialised cells, but also maintaining the normal turnover of regenerative organs, such as blood, skin or intestinal tissues.

Haematopoietic stem cells (HSCs) are multipotent stem cells that may be found, for example, in peripheral blood, bone marrow and umbilical cord blood. HSCs are capable of self-renewal and differentiation into any blood cell lineage. They are capable of recolonising the entire immune system, and the erythroid and myeloid lineages in all the haematopoietic tissues (such as bone marrow, spleen and thymus). They provide for life-long production of all lineages of haematopoietic cells.

Haematopoietic progenitor cells have the capacity to differentiate into a specific type of cell. In contrast to stem cells however, they are already far more specific: they are pushed to differentiate into their "target" cell. A difference between stem cells and progenitor cells is that stem cells can replicate indefinitely, whereas progenitor cells can only divide a limited number of times. Haematopoietic progenitor cells can be rigorously distinguished from HSCs only by functional in vivo assay (i.e. transplantation and demonstration of whether they can give rise to all blood lineages over prolonged time periods).

A differentiated cell is a cell which has become more specialised in comparison to a stem cell or progenitor cell. Differentiation occurs during the development of a multicellular organism as the organism changes from a single zygote to a complex system of tissues and cell types. Differentiation is also a common process in adults: adult stem cells divide and create fully-differentiated daughter cells during tissue repair and normal cell turnover. Differentiation dramatically changes a cell's size, shape, membrane potential, metabolic activity and responsiveness to signals. These changes are largely due to highly-controlled modifications in gene expression. In other words a differentiated cell is a cell which has specific structures and performs certain functions due to a developmental process which involves the activation and deactivation of specific genes. Here, a differentiated cell includes differentiated cells of the haematopoietic lineage such as monocytes, macrophages, neutrophils, basophils, eosinophils, erythrocytes, megakaryocytes/platelets, dendritic cells, T-cells, B-cells and NK-cells. For example, differentiated cells of the haematopoietic lineage can be distinguished from stem cells and progenitor cells by detection of cell surface molecules which are not expressed or are expressed to a lesser degree on undifferentiated cells. Examples of suitable human lineage markers include CD33, CD13, CD14, CD15 (myeloid), CD19, CD20, CD22, CD79a (B), CD36, CD71, CD235a (erythroid), CD2, CD3, CD4, CD8 (T), CD56 (NK).

HSC Source

In one embodiment of the present invention the starting population of cells comprising haematopoietic stem cells is obtained from a tissue sample.

For example, HSCs can be obtained from adult and foetal peripheral blood, umbilical cord blood, bone marrow, liver or spleen. Preferably, these cells are obtained from peripheral blood or bone marrow. They may be obtained after mobilisation of the cells in vivo by means of growth factor treatment.

Mobilisation may be carried out using, for example, G-CSF, plerixaphor or combinations thereof. Other agents, such as NSAIDs, CXCR2 ligands (Grobeta) and dipeptidyl peptidase inhibitors may also be useful as mobilising agents.

With the availability of the stem cell growth factors GM-CSF and G-CSF, most haematopoietic stem cell transplantation procedures are now performed using stem cells collected from the peripheral blood, rather than from the bone marrow. Collecting peripheral blood stem cells provides a bigger graft, does not require that the donor be subjected to general anaesthesia to collect the graft, results in a shorter time to engraftment and may provide for a lower long-term relapse rate.

Bone marrow may be collected by standard aspiration methods (either steady-state or after mobilisation), or by using next-generation harvesting tools (e.g. Marrow Miner).

In addition, HSCs may also be derived from induced pluripotent stem cells.

HSC Characteristics

HSCs are typically of low forward scatter and side scatter profile by flow cytometric procedures. Some are metabolically quiescent, as demonstrated by Rhodamine labelling which allows determination of mitochondrial activity. HSCs may comprise certain cell surface markers such as CD34, CD45, CD133, CD90 and CD49f. They may also be defined as cells lacking the expression of the CD38 and CD45RA cell surface markers. However, expression of some of these markers is dependent upon the developmental stage and tissue-specific context of the HSC. Some HSCs called "side population cells" exclude the Hoechst 33342 dye as detected by flow cytometry. Thus, HSCs have descriptive characteristics that allow for their identification and isolation.

Negative Markers

CD38 is the most established and useful single negative marker for human HSCs.

Human HSCs may also be negative for lineage markers such as CD2, CD3, CD14, CD16, CD19, CD20, CD24, CD36, CD56, CD66b, CD271 and CD45RA. However, these markers may need to be used in combination for HSC enrichment.

By negative marker it is to be understood that human HSCs lack the expression of these markers.

Positive Markers

CD34 and CD133 are the most useful positive markers for HSCs.

Some HSCs are also positive for lineage markers such as CD90, CD49f and CD93. However, these markers may need to be used in combination for HSC enrichment.

By positive marker it is to be understood that human HSCs express these markers.

Accordingly, the therapeutic population of cells may be $CD34^+CD38^-$. Further separations may be carried out to obtain, for example, $CD34^+CD38^-CD45RA^-CD90^+CD49f^+$ cells.

Separation of Cells

Separating a population of cells refers to the purification of a population of cells that exhibit a specific phenotype or characteristic from other cells which do not exhibit that phenotype or characteristic, or exhibit it to a lesser degree. For example, a population of cells that do not express a specific marker (such as CD38) may be separated from a starting population of cells. Alternatively, or in addition, a population of cells that does express another marker (such as CD34) may be separated.

In one embodiment of the present invention the method comprises the steps of:

a. separating CD38-expressing cells from a starting population of cells comprising haematopoietic stem cells;
b. separating CD34-expressing cells from the population of cells obtained in step (a) that do not express CD38;
c. transducing the CD34-expressing cell population obtained in step (b) with a vector to obtain the therapeutic cell population.

Separating a population of cells expressing a specific marker (e.g. CD38 or CD34) may be achieved by using an agent that binds to that marker.

In another embodiment the method comprises the steps of:

a. contacting a starting population of cells comprising haematopoietic stem cells with an agent reactive for CD38;
b. separating the CD38-reactive cells from the CD38-non-reactive cells;
c. contacting the CD38-non-reactive cells obtained in step (b) with an agent reactive for CD34;
d. separating the CD34-reactive cells from the CD34-non-reactive cells wherein the CD34-reactive cells form the transduction cell population;
e. transducing the transduction cell population with a vector to obtain the therapeutic cell population.

An agent reactive for a specific marker, such as CD38 or CD34, is to be understood as an agent that binds substantially specifically to that marker.

In one embodiment of the present invention the agents reactive for CD38 or CD34 are anti-CD38 or anti-CD34 antibodies, respectively.

Antibodies, as used herein, refers to complete antibodies or antibody fragments capable of binding to a selected target, and including Fv, ScFv, F(ab') and F(ab')$_2$, monoclonal and polyclonal antibodies, engineered antibodies including chimeric, CDR-grafted and humanised antibodies, and artificially selected antibodies produced using phage display or alternative techniques.

In addition, alternatives to classical antibodies may also be used in the invention, for example "avibodies", "avimers", "anticalins", "nanobodies" and "DARPins".

Accordingly, CD38-reactive cells, for example, are to be understood as those cells which express the CD38 marker and therefore bind to a CD38-reactive agent. Conversely, CD38-non-reactive cells substantially do not bind to a CD38 reactive agent. The same understanding can be applied to CD34-reactive and non-reactive cells by analogy.

The agents reactive for specific markers may be labelled so as to be identifiable using any of a number of techniques known in the art. The reactive agent may be inherently labelled, or may be modified by conjugating a label thereto. By conjugating it is to be understood that the reactive agent and label are operably linked. This means that the reactive agent and label are linked together in a manner which enables both to carry out their function (e.g. binding to a marker, allowing fluorescent identification, or allowing separation when placed in a magnetic field) substantially unhindered. Suitable methods of conjugation are well known in the art and would be readily identifiable by the skilled person.

A label may allow, for example, the labelled agent and any cell to which it is bound to be purified from its environment (e.g. the reactive agent may be labelled with a magnetic bead, or an affinity tag, such as avidin), detected or both. Detectable markers suitable for use as a label include fluorophores (e.g. green, cherry, cyan and orange fluorescent proteins) and peptide tags (e.g. a His tag, Myc tag, FLAG tag and HA tag).

In one embodiment of the present invention the anti-CD38 and/or anti-CD34 antibodies are conjugated to magnetic beads.

In another embodiment the anti-CD38 and/or anti-CD34 antibodies are conjugated to detectable markers.

In another embodiment the detectable markers are fluorophores.

A number of techniques for separating a population of cells expressing a specific marker are known in the art. These include magnetic bead-based separation technologies (e.g. closed-circuit magnetic bead-based separation), flow cytometry, fluorescence-activated cell sorting (FACS), affinity tag purification (e.g. using affinity columns or beads, such biotin columns to separate avidin-labelled agents) and microscopy-based techniques.

In one embodiment the CD38-expressing cells and/or CD34-expressing cells are separated using magnetic bead-based separation or flow cytometry.

In another embodiment the CD38-reactive cells and/or CD34-reactive cells are separated using magnetic bead-based separation or flow cytometry.

It may also be possible to perform the separation using a combination of different techniques, such as a magnetic bead-based separation step followed by sorting of the resulting population of cells for one or more additional (positive or negative) markers by flow cytometry.

Clinical grade separation may be performed, for example, using the CliniMACS® system (Miltenyi). This is an example of a closed-circuit magnetic bead-based separation technology.

It is also envisaged that dye exclusion properties (e.g. side population or rhodamine labelling) or enzymatic activity (e.g. ALDH activity) may be used to enrich for HSCs.

When using current magnetic bead-based separation technology it is preferred that the negative separation step (i.e. the depletion of CD38-expressing cells) should precede the positive separation step (i.e. the enrichment of CD34-expressing cells). However, it is envisaged that it may be possible to carry out both negative and positive separation steps simultaneously with alternative techniques, for example advanced flow cytometry techniques (e.g. closed-circuit FACS).

It is, however, also possible to carry out the positive separation step (i.e. the enrichment of CD34-expressing cells) before the negative separation step (i.e. the depletion of CD38-expressing cells).

The populations of cells of the invention may be separated into fractions according to CD38 expression levels. CD38 expression levels may be quantified using suitable techniques known in the art, for example flow cytometry techniques (see, for example, FIG. 4). For example, the CD38 expression level may be measured by antibody staining with the IB6 clone or similar/equivalent reagents.

The amount of CD38 expression by a cell may be represented by a percent expression level, 0% being the lowest and 100% being the highest expressing cell.

A population of cells may be categorised or separated into sub-populations (e.g. sub-populations which are derived from a $CD34^+$ population) based on CD38 expression level.

The population of cells may be categorised or separated into $CD38^-$, $CD38^{int1}$, $CD38^{int2}$ or $CD38^+$ sub-populations which have increasing levels of CD38 expression in that order (e.g. the whole $CD34^+$ population is ranked according to CD38 expression/staining intensity). For example (when pre-gating the analysis on $CD34^+$ cells), a population of cells with a $CD38^-$ phenotype may be contained within the lowest 10% of cells, based on CD38 expression level; a population of cells with a $CD38^{int1}$ phenotype (also referred to as $CD38^{int/lo}$) may be contained within the next highest 30% of cells to the $CD38^-$ cells; a population of cells with a $CD38^{int2}$ phenotype (also referred to as $CD38^{+/int}$) may be contained within the next highest 30% of cells to the $CD38^{int1}$ cells; and a population of cells with a $CD38^+$ phenotype (also referred to as $CD38^{hi}$) may be contained within the next highest 30% of cells to the $CD38^{int2}$ cells.

Thus, a population of cells with a $CD38^-$ phenotype may be, for example, contained within the about 0-12% range of CD38 expression, for example the about 0-10% range.

A population of cells with a $CD38^{int1}$ phenotype (also referred to as $CD38^{int/lo}$) may be, for example, contained within the about 10-40% range of CD38 expression, for example the about 12-40% or the about 13-40% range.

A population of cells with a $CD38^{int2}$ phenotype (also referred to as $CD38^{+/int}$) may be, for example, contained within the about 40-70% range of CD38 expression, for example the about 41-70% range.

A population of cells with a $CD38^+$ (also referred to as $CD38^{hi}$) phenotype may be, for example, contained within the about 70-100% range of CD38 expression, for example the about 71-100% range.

The person skilled in the art would readily be able to select a population of cells based on CD38 expression level depending on the intended use, based on the disclosure herein. Indeed, the person skilled in the art would readily appreciate the disclosed levels of CD38 expression may be slightly adjusted depending on the desired use.

In a preferred embodiment, the $CD38^-$ population (stem cell-containing fraction) is defined as having the 0-10% range of CD38 expression; the $CD38^{int1}$ population (multipotent progenitor-containing fraction with short- to intermediate-term repopulating capacity) is defined as having the 10-40% range of CD38 expression; the $CD38^{int2}$ population (progenitor-containing fraction with short-term repopulating capacity) is defined as having the 40-70% range of CD38 expression; and the $CD38^+$ population (precursor cells substantially devoid of significant repopulating capacity) is defined as having the 70-100% range of CD38 expression.

These fractions of cells may also be combined as necessary. For example, the $CD38^{int1}$ and the $CD38^{int2}$ fractions may be combined to form a $CD38^{int}$ fraction (contained within the about 10-70% range of CD38 expression); and the $CD38^{int1}$, $CD38^{int2}$ and $CD38^+$ groups may be combined to form a $CD38^{low-intm-high}$ (also referred to as $CD38^{int/+}$) fraction (contained within the about 10-100% range of CD38 expression, for example the about 12-100% or the about 13-100% range).

Vectors

A vector is a tool that allows or facilitates the transfer of an entity from one environment to another. In accordance with the present invention, and by way of example, some vectors used in recombinant nucleic acid techniques allow entities, such as a segment of nucleic acid (e.g. a heterologous DNA segment, such as a heterologous cDNA segment), to be transferred into a target cell. The vector may serve the purpose of maintaining the heterologous nucleic acid (DNA or RNA) within the cell, facilitating the replication of the vector comprising a segment of nucleic acid, or facilitating the expression of the protein encoded by a segment of nucleic acid. Vectors may be non-viral or viral. Examples of vectors used in recombinant nucleic acid techniques include, but are not limited to, plasmids, chromosomes, artificial chromosomes and viruses. The vector may also be, for example, a naked nucleic acid (e.g. DNA). In its simplest form, the vector may itself be a nucleotide of interest.

The vectors used in the invention may be, for example, plasmid or virus vectors and may include a promoter for the expression of a polynucleotide and optionally a regulator of the promoter.

Vectors comprising polynucleotides used in the invention may be introduced into cells using a variety of techniques known in the art, such as transformation and transduction. Several techniques are known in the art, for example infection with recombinant viral vectors, such as retroviral, lentiviral, adenoviral, adeno-associated viral, baculoviral and herpes simplex viral vectors; direct injection of nucleic acids and biolistic transformation.

Non-viral delivery systems include but are not limited to DNA transfection methods. Here, transfection includes a process using a non-viral vector to deliver a gene to a target cell.

Typical transfection methods include electroporation, DNA biolistics, lipid-mediated transfection, compacted DNA-mediated transfection, liposomes, immunoliposomes, lipofectin, cationic agent-mediated transfection, cationic facial amphiphiles (CFAs) (Nature Biotechnology 1996 14; 556) and combinations thereof.

In addition, the invention may employ gene targeting protocols, for example the delivery of DNA-modifying agents.

Viral Vectors

In one embodiment a viral vector is used in the present invention.

In another embodiment the viral vector is a retroviral, adenoviral or adeno-associated viral vector.

In another embodiment the retroviral vector is a lentiviral vector.

Retro Viral and Lentiviral Vectors

The retroviral vector used in the present invention may be derived from or may be derivable from any suitable retrovirus. A large number of different retroviruses have been identified. Examples include: murine leukemia virus (MLV), human T-cell leukemia virus (HTLV), mouse mammary tumour virus (MMTV), Rous sarcoma virus (RSV), Fujinami sarcoma virus (FuSV), Moloney murine leukemia virus (Mo MLV), FBR murine osteosarcoma virus (FBR MSV), Moloney murine sarcoma virus (Mo-MSV), Abelson murine leukemia virus (A-MLV), Avian myelocytomatosis virus-29 (MC29) and Avian erythroblastosis virus (AEV). A detailed list of retroviruses may be found in Coffin et al. (1997) "Retroviruses", Cold Spring Harbour Laboratory Press Eds: J M Coffin, S M Hughes, H E Varmus pp 758-763.

Retroviruses may be broadly divided into two categories, namely "simple" and "complex". Retroviruses may even be further divided into seven groups. Five of these groups represent retroviruses with oncogenic potential. The remaining two groups are the lentiviruses and the spumaviruses. A review of these retroviruses is presented in Coffin et al (1997) ibid.

The basic structure of retrovirus and lentivirus genomes share many common features such as a 5' LTR and a 3' LTR, between or within which are located a packaging signal to enable the genome to be packaged, a primer binding site, integration sites to enable integration into a host cell genome and gag, pol and env genes encoding the packaging components—these are polypeptides required for the assembly of viral particles. Lentiviruses have additional features, such as rev and RRE sequences in HIV, which enable the efficient export of RNA transcripts of the integrated provirus from the nucleus to the cytoplasm of an infected target cell.

In the provirus, these genes are flanked at both ends by regions called long terminal repeats (LTRs). The LTRs are responsible for proviral integration and transcription. LTRs also serve as enhancer-promoter sequences and can control the expression of the viral genes.

The LTRs themselves are identical sequences that can be divided into three elements, which are called U3, R and U5. U3 is derived from the sequence unique to the 3' end of the RNA. R is derived from a sequence repeated at both ends of the RNA and U5 is derived from the sequence unique to the 5' end of the RNA. The sizes of the three elements can vary considerably among different retroviruses.

In a defective retroviral vector genome gag, pol and env may be absent or not functional. The R regions at both ends of the RNA are repeated sequences. U5 and U3 represent unique sequences at the 5' and 3' ends of the RNA genome respectively.

In a typical retroviral vector used in the present invention, at least part of one or more protein coding regions essential for replication may be removed from the virus. This makes the viral vector replication-defective. Portions of the viral genome may also be replaced by a library encoding candidate modulating moieties operably linked to a regulatory control region and a reporter moiety in the vector genome in order to generate a vector comprising candidate modulating moieties which is capable of transducing a target non-dividing host cell and/or integrating its genome into a host genome.

Lentivirus vectors are part of a larger group of retroviral vectors. A detailed list of lentiviruses may be found in Coffin et al (1997) "Retroviruses" Cold Spring Harbour Laboratory Press Eds: J M Coffin, S M Hughes, H E Varmus pp 758-763. In brief, lentiviruses can be divided into primate and non-primate groups. Examples of primate lentiviruses include but are not limited to: the human immunodeficiency virus (HIV), the causative agent of human auto-immunodeficiency syndrome (AIDS), and the simian immunodeficiency virus (SIV). The non-primate lentiviral group includes the prototype "slow virus" visna/maedi virus (VMV), as well as the related caprine arthritis-encephalitis virus (CAEV), equine infectious anaemia virus (EIAV) and the more recently described feline immunodeficiency virus (FIV) and bovine immunodeficiency virus (BIV).

The lentivirus family differs from retroviruses in that lentiviruses have the capability to infect both dividing and non-dividing cells (Lewis et al (1992) EMBO J 11(8):3053-3058 and Lewis and Emerman (1994) J Virol 68 (1):510-516). In contrast, other retroviruses, such as MLV, are unable to infect non-dividing or slowly dividing cells such as those that make up, for example, muscle, brain, lung and liver tissue.

A lentiviral vector, as used herein, is a vector which comprises at least one component part derivable from a lentivirus. Preferably, that component part is involved in the biological mechanisms by which the vector infects cells, expresses genes or is replicated.

The lentiviral vector may be a "non-primate" vector, i.e. derived from a virus which does not primarily infect primates, especially humans.

Examples of non-primate lentivirus may be any member of the family of lentiviridae which does not naturally infect a primate and may include a feline immunodeficiency virus (FIV), a bovine immunodeficiency virus (BIV), a caprine arthritis encephalitis virus (CAEV), a Maedi visna virus (MVV) or an equine infectious anaemia virus (EIAV).

The viral vector may be derived from EIAV. EIAV has the simplest genomic structure of the lentiviruses. In addition to the gag, pol and env genes, EIAV encodes three other genes: tat, rev, and S2. Tat acts as a transcriptional activator of the viral LTR (Derse and Newbold (1993) Virology 194(2):530-536 and Maury et al (1994) Virology 200(2):632-642) and rev regulates and coordinates the expression of viral genes through rev-response elements (RRE) (Martarano et al. (1994) J Virol 68(5):3102-3111). The mechanisms of action of these two proteins are thought to be broadly similar to the analogous mechanisms in the primate viruses (Martarano et al. (1994) J Virol 68(5):3102-3111). The function of S2 is unknown. In addition, an EIAV protein, Ttm, has been identified that is encoded by the first exon of tat spliced to the env coding sequence at the start of the transmembrane protein.

Preferably the viral vector used in the present invention has a minimal viral genome.

As used herein, the term "minimal viral genome" means that the viral vector has been manipulated so as to remove the non-essential elements and to retain the essential elements in order to provide the required functionality to infect, transduce and deliver a nucleotide sequence of interest to a target host cell. Further details of this strategy can be found in WO 1998/017815.

However, the plasmid vector used to produce the viral genome within a host cell/packaging cell will include transcriptional regulatory control sequences operably linked to the retroviral genome to direct transcription of the genome in a host cell/packaging cell. These regulatory sequences may be the natural sequences associated with the transcribed retroviral sequence, i.e. the 5' U3 region, or they may be a heterologous promoter such as another viral promoter, for example the CMV promoter. Some lentiviral genomes require additional sequences for efficient virus production. For example, particularly in the case of HIV, rev and RRE sequences may be included. However the requirement for rev and RRE may be reduced or eliminated by codon optimisation. Further details of this strategy can be found in WO 2001/079518. Alternative sequences which perform the same function as the rev/RRE system are also known. For example, a functional analogue of the rev/RRE system is found in the Mason Pfizer monkey virus. This is known as the constitutive transport element (CTE) and comprises an RRE-type sequence in the genome which is believed to interact with a factor in the infected cell. The cellular factor can be thought of as a rev analogue. Thus, CTE may be used as an alternative to the rev/RRE system. Any other functional equivalents which are known or become available may be relevant to the invention. For example, it is also known that the Rex protein of HTLV-I can functionally replace the Rev protein of HIV-1. Rev and RRE may be absent or non-functional in the vector for use in the methods of the present invention; in the alternative rev and RRE may be present.

The vectors for use in the methods of the present invention may use a self-inactivating (SIN) vector in which the viral enhancer and promoter sequences have been deleted. SIN vectors can be generated and transduce non-dividing cells in vivo with an efficacy similar to that of wild-type vectors. The transcriptional inactivation of the long terminal repeat (LTR) in the SIN provirus should prevent mobilisation by replication-competent virus. This should also enable the regulated expression of genes from internal promoters by eliminating any cis-acting effects of the LTR.

By way of example, self-inactivating retroviral vector systems have been constructed by deleting the transcriptional enhancers or the enhancers and promoter in the U3 region of the 3' LTR. After a round of vector reverse transcription and integration, these changes are copied into both the 5' and the 3' LTRs producing a transcriptionally inactive provirus. However, any promoter(s) internal to the LTRs in such vectors will still be transcriptionally active. This strategy has been employed to eliminate effects of the enhancers and promoters in the viral LTRs on transcription from internally placed genes. Such effects include increased transcription or suppression of transcription. This strategy can also be used to eliminate downstream transcription from the 3' LTR into genomic DNA. This is of particular concern in human gene therapy where it may be important to prevent the adventitious activation of an endogenous oncogene. Yu et al., (1986) PNAS 83: 3194-98; Marty et al., (1990) Biochimie 72: 885-7; Naviaux et al., (1996) J. Virol. 70: 5701-5; Iwakuma et al., (1999) Virol. 261: 120-32; Deglon et al., (2000) Human Gene Therapy 11: 179-90.

Non-Replicating Lentiviral Vectors

In a replication-defective lentiviral vector genome gag, pol and env may be absent or not functional.

In a typical lentiviral vector used in the present invention, at least part of one or more protein coding regions essential for replication may be removed from the virus. This makes the viral vector replication-defective. Portions of the viral genome may also be replaced by a nucleotide of interest (NOI) in order to generate a vector comprising an NOI which is capable of transducing a target non-dividing host cell and/or integrating its genome into a host genome.

In one embodiment the lentiviral vectors are non-integrating vectors as described in WO 2007/071994.

The lentiviral vector may be a "non-primate" vector, i.e., derived from a virus which does not primarily infect primates, especially humans.

Adenoviral Vectors

In another embodiment of the present invention, the vector may be an adenovirus vector. The adenovirus is a double-stranded, linear DNA virus that does not go through an RNA intermediate. There are over 50 different human serotypes of adenovirus divided into 6 subgroups based on the genetic sequence homology. The natural targets of adenovirus are the respiratory and gastrointestinal epithelia, generally giving rise to only mild symptoms. Serotypes 2 and 5 (with 95% sequence homology) are most commonly used in adenoviral vector systems and are normally associated with upper respiratory tract infections in the young.

Adenoviruses are non-enveloped regular icosahedrons. A typical adenovirus comprises a 140 nm encapsidated DNA virus. The icosahedral symmetry of the virus is composed of 152 capsomeres: 240 hexons and 12 pentons. The core of the particle contains the 36 kb linear duplex DNA which is covalently associated at the 5' ends with the Terminal Protein (TP) which acts as a primer for DNA replication. The DNA has inverted terminal repeats (ITR) and the length of these varies with the serotype.

The adenovirus is capable of in vivo and in vitro transduction of a broad range of cell types of human and non-human origin. These cells include respiratory airway epithelial cells, hepatocytes, muscle cells, cardiac myocytes, synoviocytes, primary mammary epithelial cells and post-mitotically terminally differentiated cells such as neurons.

Adenoviral vectors are also capable of transducing non-dividing cells. This is very important for diseases, such as cystic fibrosis, in which the affected cells in the lung epithelium have a slow turnover rate. In fact, several trials are underway utilising adenovirus-mediated transfer of cystic fibrosis transporter (CFTR) into the lungs of afflicted adult cystic fibrosis patients.

Adenoviruses have been used as vectors for gene therapy and for expression of heterologous genes. The large (36 kb) genome can accommodate up to 8 kb of foreign insert DNA and is able to replicate efficiently in complementing cell lines to produce very high titres of up to 1012. Adenovirus is thus one of the best systems to study the expression of genes in primary non-replicative cells.

The expression of viral or foreign genes from the adenovirus genome does not require a replicating cell. Adenoviral vectors enter cells by receptor mediated endocytosis. Once inside the cell, adenovirus vectors rarely integrate into the host chromosome. Instead, they function episomally (independently from the host genome) as a linear genome in the host nucleus. Hence the use of recombinant adenovirus alleviates the problems associated with random integration into the host genome.

Adeno-Associated Virus Vectors

Adeno-associated virus (AAV) is an attractive vector system for use in the present invention as it has a high frequency of integration and it can infect non-dividing cells. This makes it useful for delivery of genes into mammalian cells in tissue culture. AAV has a broad host range for infectivity. Details concerning the generation and use of rAAV vectors are described in U.S. Pat. Nos. 5,139,941 and 4,797,368.

Recombinant AAV vectors have been used successfully for in vitro and in vivo transduction of marker genes and genes involved in human diseases.

Herpes Simplex Virus Vectors

Herpes simplex virus (HSV) is an enveloped double-stranded DNA virus that naturally infects neurons. It can accommodate large sections of foreign DNA, which makes it attractive as a vector system, and has been employed as a vector for gene delivery to neurons.

The use of HSV in therapeutic procedures will require the strains to be attenuated so that they cannot establish a lytic cycle. In particular, if HSV vectors are to be used for gene therapy in humans, the polynucleotide should preferably be inserted into an essential gene. This is because if a vector virus encounters a wild-type virus, transfer of a heterologous gene to the wild-type virus could occur by recombination. However, as long as the polynucleotide is inserted into an essential gene, this recombinational transfer would also delete the essential gene in the recipient virus and prevent "escape" of the heterologous gene into the replication competent wild-type virus population.

Nucleotide of Interest

The vector used in the present invention preferably comprises a nucleotide of interest.

Preferably the nucleotide of interest gives rise to a therapeutic effect.

Suitable NOIs include, but are not limited to sequences encoding enzymes, cytokines, chemokines, hormones, antibodies, anti-oxidant molecules, engineered immunoglobulin-like molecules, single chain antibodies, fusion proteins, immune co-stimulatory molecules, immunomodulatory molecules, anti-sense RNA, microRNA, shRNA, siRNA, ribozymes, miRNA target sequences, a transdomain negative mutant of a target protein, toxins, conditional toxins, antigens, tumour suppressor proteins, growth factors, transcription factors, membrane proteins, surface receptors, anti-cancer molecules, vasoactive proteins and peptides, antiviral proteins and ribozymes, and derivatives thereof (such as derivatives with an associated reporter group). The NOIs may also encode pro-drug activating enzymes.

An examples of a NOI is the beta-globin chain which may be used for gene therapy of thalassemia/sickle cell disease.

NOIs also include those useful for the treatment of other diseases requiring non-urgent/elective gene correction in the myeloid lineage such as: chronic granulomatous disease (CGD, e.g. the gp91phox transgene), leukocyte adhesion defects, other phagocyte disorders in patients without ongoing severe infections and inherited bone marrow failure syndromes (e.g. Fanconi anaemia), as well as primary immunodeficiencies (SCIDs).

Support Cell Population

Our unexpected finding that highly purified HSCs are significantly more transducible by vectors, particularly lentiviral vectors, prompted us to evaluate a radically new design of the HSC gene therapy protocol. The new protocol comprises the separation of a starting cell population (e.g. one obtained from mobilised peripheral blood, bone marrow or umbilical cord blood) into an HSC-enriched fraction (the therapeutic cell population, for example having an HSC content enriched with respect to $CD34^+$ cells) and a progenitor containing fraction (a support cell population). The latter may be frozen without ex vivo manipulation, and may be infused into a subject to boost haematologic recovery after myeloablative conditioning. The highly purified, HSC containing fraction will be transduced using the "minimal" ex vivo culture as described herein, reducing culture time and vector dose with respect to the standard $CD34^+$ cell transduction protocol.

In one embodiment of the present invention the separated CD38-expressing cells or CD38-reactive cells or portion thereof are retained to form a support cell population. This population may comprise the $CD38^{int1}$, $CD38^{int2}$ and/or $CD38^+$ fractions.

The therapeutic and/or support cell populations may be frozen after their preparation to facilitate storage before later transplantation. As the support cell population is separated at an early stage of the method for preparing the therapeutic cell population, it is preferred that it should be frozen as soon as possible after separation, preferably immediately after separation. Methods of freezing cells to maintain their viability are well known in the art.

Frozen cells may be thawed when required for use, for example for administration to a subject.

Cell Transduction

Transduction of a population of cells with a vector may utilise a pre-stimulation phase prior to a second phase of culture during which the cells are exposed to the vector. During the pre-stimulation phase, the cells may be cultured in culture medium comprising, for example, stem cell factor (SCF), FLT3 ligand (FLT3L) and thrombopoietin (TPO), and optionally IL3, IL6, IL11, M-CSF, FGF-1, IGF-2, IGFBP2, ANGPTL3 or 5.

The population of cells may, for example, be the therapeutic cell population as described herein, a population of $CD34^+CD38^-$ cells, a population of haematopoietic stem cells or a population of haematopoietic progenitor cells.

Preferably, the vector is a lentiviral vector.

Either the standard or short protocol described below may be implemented during the methods described herein. However it will also be appreciated that both the standard and short protocols may be implemented during any method of transducing a population of cells with a vector (e.g. a lentiviral vector). This provides further aspects to the present invention.

Transduction of a population of cells with a vector may be carried out using a standard protocol in which the cells undergo 44 h or more of culture before administration to a subject.

The present invention therefore provides methods in which the step of transducing a population of cells with a vector comprises culturing the cells for about 44 h or more ("standard" protocol). The "step of transducing a population of cells with a vector" is to be understood as the pre-stimulation and vector exposure phases.

For example, the population of cells may be cultured for about 44-66 h, 44-60 h, 44-54 h or 44-48 h during the step of transduction with a vector. In one embodiment the population of cells is cultured for about 66, 60, 54, 48 or 44 h during the step of transduction with a vector.

The present inventors have found, however, that culture time negatively influences functional engraftment capacity of both haematopoietic stem and progenitor cells. Accordingly, the present inventors have developed short transduction protocols which balance the improvement in engraftment with the corresponding reduction in transduction efficiency.

The present invention therefore provides methods in which the step of transducing a population of cells with a vector comprises culturing the cells for less than about 44 h ("short" protocol).

For example, the population of cells may be cultured for about 12-42 h, 12-36 h, 12-24 h or 12-18 h during the step of transduction with a vector. In one embodiment the population of cells is cultured for about 42, 36, 30, 24, 18 or 12 h during the step of transduction with a vector. Preferably the population of cells is cultured for about 24 h during the step of transduction with a vector.

In either the standard or short protocol, the pre-stimulation phase may, for example, be about 12, 14, 16, 18 or 22 h duration. Preferably, the pre-stimulation phase is of about 16 h duration.

In either the standard or short protocol, the vector exposure phase may, for example, be about 8, 10, 12, 14 or 16 h duration. Preferably, the vector exposure phase is of about 8 h duration.

In either the standard or short protocol, the step of transducing a population of cells with a vector may comprise repeating the pre-stimulation and vector exposure phases before administration of the cells to a subject. For example, the cells may undergo pre-stimulation, followed by vector exposure, followed by a second pre-stimulation phase, followed by a second vector exposure phase.

Preferably, the cell culture medium during the step of transducing a population of cells with a vector does not comprise IL3.

Prostaglandin E2 or a prostaglandin E2 derivative (e.g. 16,16-dimethyl prostaglandin E2 (dmPGE2)) may be added to the population of cells during the pre-stimulation phase. Prostaglandin E2 or the prostaglandin E2 derivative may be added at the start of the pre-stimulation phase, or during the pre-stimulation phase. For example, prostaglandin E2 or the prostaglandin E2 derivative may be added about 1, 2, 3, 4, 5, 6, 7, 8, 9, 10, 11 or 12 h before the exposure of the population of cells to the vector. Preferably, the prostaglandin E2 or the prostaglandin E2 derivative is added to the population of cells during the pre-stimulation phase, about 2 h before the exposure of the cells to the vector. In another embodiment the prostaglandin E2 or the prostaglandin E2 derivative is added to the population of cells at the same time as exposure to the vector.

Preferred transduction protocols are set out in Example 8.

Pharmaceutical Composition

The present invention provides a pharmaceutical composition comprising the therapeutic cell population and/or support cell population of the invention.

The cells of the present invention may be formulated for administration to subjects with a pharmaceutically acceptable carrier, diluent or excipient. Suitable carriers and diluents include isotonic saline solutions, for example phosphate-buffered saline, and potentially contain human serum albumin.

Handling of the cell therapy product is preferably performed in compliance with FACT-JACIE International Standards for cellular therapy.

Hematopoietic Stem Cell Transplantation

The present invention provides a therapeutic cell population for use in medicine, for example for use in gene therapy.

The use may be as part of a haematopoietic stem cell transplantation procedure.

Hematopoietic stem cell transplantation (HSCT) is the transplantation of blood stem cells derived from the bone marrow (in this case known as bone marrow transplantation) or blood. Stem cell transplantation is a medical procedure in the fields of haematology and oncology, most often performed for people with diseases of the blood or bone marrow, or certain types of cancer.

Many recipients of HSCTs are multiple myeloma or leukemia patients who would not benefit from prolonged treatment with, or are already resistant to, chemotherapy. Candidates for HSCTs include paediatric cases where the patient has an inborn defect such as severe combined immunodeficiency or congenital neutropenia with defective stem cells, and also children or adults with aplastic anaemia who have lost their stem cells after birth. Other conditions treated with stem cell transplants include sickle-cell disease, myelodysplastic syndrome, neuroblastoma, lymphoma, Ewing's Sarcoma, Desmoplastic small round cell tumor and Hodgkin's disease. More recently non-myeloablative, or so-called "mini transplant", procedures have been developed that require smaller doses of preparative chemotherapy and radiation. This has allowed HSCT to be conducted in the elderly and other patients who would otherwise be considered too weak to withstand a conventional treatment regimen.

In one embodiment of the present invention the therapeutic cell population is administered in combination with the support cell population of the invention.

In one embodiment the therapeutic cell population and/or support cell population of the invention is administered as part of an autologous stem cell transplant procedure.

In another embodiment the therapeutic cell population and/or support cell population of the invention is administered as part of an allogeneic stem cell transplant procedure.

By autologous stem cell transplant procedure it is to be understood that the starting population of cells (from which the therapeutic and/or support cell populations are derived) is obtained from the same subject as that to which the therapeutic and/or support cell populations are administered. As discussed previously, autologous transplant procedures are advantageous as they avoid problems associated with immunological incompatibility and are available to subjects irrespective of the availability of a genetically matched donor.

By allogeneic stem cell transplant procedure it is to be understood that the starting population of cells (from which the therapeutic and/or support cell populations are derived) is obtained from a different subject as that to which the therapeutic and/or support cell populations are administered. Preferably, the donor will be genetically matched to the subject to which the cells are administered to minimise the risk of immunological incompatibility.

In one embodiment of the present invention the therapeutic cell population is administered to a subject prior to administration of the support cell population.

The therapeutic cell population may be administered to a subject, for example, about 1-72, 12-60 or 24-48 h prior to administration of the support cell population, such as about 1, 2, 3, 4, 5, 6, 12, 18, 24, 30, 36, 42, 48, 60 or 72 h prior to administration of the support cell population.

In another embodiment the therapeutic cell population is administered to a subject contemporaneously with or simultaneously to administration of the support cell population.

Suitable doses of therapeutic and support cell populations are such as to be therapeutically and/or prophylactically effective. The dose to be administered may depend on the subject and condition to be treated, and may be readily determined by a skilled person.

A possible dose of $CD34^+CD38^+$ cells within the support cell population may be approximately 4-5 million cells/kg. This dose should ensure timely short-term engraftment after myeloablative conditioning.

Accordingly, as the support cell population of the invention is not enriched for $CD34^+$ cells, a possible target dose of the support cell population may be approximately 50-1000 million $CD38^+$ nucleated cells/kg, such as about 100 million cells/kg (assuming a $CD34^+$ cell concentration of 5%). For example, a possible dose of cells derived from mobilised peripheral blood may be about 100-500 million cells/kg, while a possible dose of cells derived from bone marrow may be about 50-200 million cells/kg.

A possible dose of the therapeutic cell population may be approximately 0.1-2 million cells/kg, for example about 0.5-1 million cells/kg.

The overall ratio of the therapeutic:support cell populations depends on the clinical context and on the way the support cell population is prepared. In a case where the support cell population is prepared by CD38 selection (e.g. of leukapheresis or bone marrow harvest) without prior CD34 enrichment, the overall ratio of therapeutic:support cell population may be approximately 1:100-1:1000, for example about 1:500 or 1:100. It is preferable to dose the support cell population based on the absolute number of $CD34^+$ cells contained within (independently of whether $CD34^+$ pre-enrichment has been performed or not).

In one embodiment, when the subject has undergone myeloablative conditioning, the doses of cells may be adjusted such that the number of $CD34^+$ cells administered in the support cell population is about 5-15×, preferably 5-10× the number of $CD34^+$ cells administered in the therapeutic cell population. Thus, for example, the ratio of $CD34^+CD38^-$ cells to uncultured $CD34^+CD38^+$ progenitor cells administered to a subject may be about 1:10 or 1:5.

The support cell population to be administered may comprise a minimum absolute number of about 2.5-3 million $CD34^+$ cells/kg patient weight.

When a subject has not undergone myeloablative conditioning, the therapeutic cell population may be administered alone to the subject (i.e. the support cell population may not be required).

The therapeutic and/or support cell populations of the present invention may be useful in the treatment of the disorders listed in WO 1998/005635. For ease of reference, part of that list is now provided: cancer, inflammation or inflammatory disease, dermatological disorders, fever, cardiovascular effects, haemorrhage, coagulation and acute phase response, cachexia, anorexia, acute infection, HIV infection, shock states, graft-versus-host reactions, autoimmune disease, reperfusion injury, meningitis, migraine and aspirin-dependent anti-thrombosis; tumour growth, invasion and spread, angiogenesis, metastases, malignant, ascites and malignant pleural effusion; cerebral ischaemia, ischaemic heart disease, osteoarthritis, rheumatoid arthritis, osteoporosis, asthma, multiple sclerosis, neurodegeneration, Alzheimer's disease, atherosclerosis, stroke, vasculitis, Crohn's disease and ulcerative colitis; periodontitis, gingivitis; psoriasis, atopic dermatitis, chronic ulcers, epidermolysis bullosa; corneal ulceration, retinopathy and surgical wound healing; rhinitis, allergic conjunctivitis, eczema, anaphylaxis; restenosis, congestive heart failure, endometriosis, atherosclerosis or endosclerosis.

In addition, or in the alternative, the therapeutic and/or support cell populations of the present invention may be useful in the treatment of the disorders listed in WO 1998/007859. For ease of reference, part of that list is now provided: cytokine and cell proliferation/differentiation activity; immunosuppressant or immunostimulant activity (e.g. for treating immune deficiency, including infection with human immune deficiency virus; regulation of lymphocyte growth; treating cancer and many autoimmune diseases, and to prevent transplant rejection or induce tumour immunity); regulation of haematopoiesis, e.g. treatment of myeloid or lymphoid diseases; promoting growth of bone, cartilage, tendon, ligament and nerve tissue, e.g. for healing wounds, treatment of burns, ulcers and periodontal disease and neurodegeneration; inhibition or activation of follicle-stimulating hormone (modulation of fertility); chemotactic/chemokinetic activity (e.g. for mobilising specific cell types to sites of injury or infection); haemostatic and thrombolytic activity (e.g. for treating haemophilia and stroke); antiinflammatory activity (for treating e.g. septic shock or Crohn's disease); as antimicrobials; modulators of e.g. metabolism or behaviour; as analgesics; treating specific deficiency disorders; in treatment of e.g. psoriasis, in human or veterinary medicine.

In addition, or in the alternative, the therapeutic and/or support cell populations of the present invention may be useful in the treatment of the disorders listed in WO 1998/009985. For ease of reference, part of that list is now provided: macrophage inhibitory and/or T cell inhibitory activity and thus, anti-inflammatory activity; anti-immune activity, i.e. inhibitory effects against a cellular and/or humoral immune response, including a response not associated with inflammation; inhibit the ability of macrophages and T cells to adhere to extracellular matrix components and fibronectin, as well as up-regulated fas receptor expression in T cells; inhibit unwanted immune reaction and inflammation including arthritis, including rheumatoid arthritis, inflammation associated with hypersensitivity, allergic reactions, asthma, systemic lupus erythematosus, collagen diseases and other autoimmune diseases, inflammation associated with atherosclerosis, arteriosclerosis, atherosclerotic heart disease, reperfusion injury, cardiac arrest, myocardial infarction, vascular inflammatory disorders, respiratory distress syndrome or other cardiopulmonary diseases, inflammation associated with peptic ulcer, ulcerative colitis and other diseases of the gastrointestinal tract, hepatic fibrosis, liver cirrhosis or other hepatic diseases, thyroiditis or other glandular diseases, glomerulonephritis or other renal and urologic diseases, otitis or other oto-rhino-laryngological diseases, dermatitis or other dermal diseases, periodontal diseases or other dental diseases, orchitis or epididimo-orchitis, infertility, orchidal trauma or other immune-related testicular diseases, placental dysfunction, placental insufficiency, habitual abortion, eclampsia, pre-eclampsia and other immune and/or inflammatory-related gynaecological diseases, posterior uveitis, intermediate uveitis, anterior uveitis, conjunctivitis, chorioretinitis, uveoretinitis, optic neuritis, intraocular inflammation, e.g. retinitis or cystoid macular oedema, sympathetic ophthalmia, scleritis, retinitis pigmentosa, immune and inflammatory components of degenerative fondus disease, inflammatory components of ocular trauma, ocular inflammation caused by infection, proliferative vitreo-retinopathies, acute ischaemic optic neuropathy, excessive scarring, e.g. following glaucoma filtration operation, ocular implants and other immune and inflammatory-related ophthalmic diseases, inflammation associated with autoimmune diseases or conditions or disorders where, both in the central nervous system (CNS) or in any other organ, immune and/or inflammation suppression would be beneficial, Parkinson's disease, complication and/or side effects from treatment of Parkinson's disease, AIDS-related dementia complex HIV-related encephalopathy, Devic's disease, Sydenham chorea, Alzheimer's disease and other degenerative diseases, conditions or disorders of the CNS, inflammatory components of stokes, post-polio syndrome, immune and inflammatory components of psychiatric disorders, myelitis, encephalitis, subacute sclerosing pan-encephalitis, encephalomyelitis, acute neuropathy, subacute neuropathy, chronic neuropathy, Guillaim-Barre syndrome, Sydenham chora, myasthenia gravis, pseudo-tumour cerebri, Down's Syndrome, Huntington's disease, amyotrophic lateral sclerosis, inflammatory components of CNS compression or CNS trauma or infections of the CNS, inflammatory components of muscular atrophies and dystrophies, and immune and inflammatory related diseases, conditions or disorders of the central and peripheral nervous systems, post-traumatic inflammation, septic shock, infectious diseases, inflammatory complications or side effects of surgery, bone marrow transplantation or other transplantation complications and/or side effects, inflammatory and/or immune complications and side effects of gene therapy, e.g. due to infection with a viral carrier, or inflammation associated with AIDS, to suppress or inhibit a humoral and/or cellular immune response, to treat or ameliorate monocyte or leukocyte proliferative diseases, e.g. leukaemia, by reducing the amount of monocytes or lymphocytes, for the prevention and/or treatment of graft rejection in cases of transplantation of natural or artificial cells, tissue and organs such as cornea, bone marrow, organs, lenses, pacemakers, natural or artificial skin tissue.

Kit

In another aspect, the present invention provides a kit comprising the therapeutic and support cell populations of the invention.

The therapeutic and support cell populations may be provided in suitable containers.

The kit may also include instructions for use.

Haematopoietic Progenitor Cell Transplantation

The present invention provides a haematopoietic progenitor cell population for use in gene therapy, wherein the haematopoietic progenitor cell population has been transduced with a nucleotide of interest.

As we have shown, such progenitor cells provide short term engraftment. Accordingly, such gene therapy would provide a non-permanent effect in the subject. For example, the effect may be limited to 1-6 months following administration of the transduced haematopoietic progenitor cells. An advantage of this approach would be better safety and tolerability, due to the self-limited nature of the therapeutic intervention.

Accordingly, we can tailor the persistence of gene-modified cells (see Example 3). For example, it is envisaged that different populations of cells could be administered for the treatment of different conditions depending on the length of time over which expression of the nucleotide of interest is desired, such as:
1. Long term: $CD34^+CD38^-$ cells (e.g. 0-10% percentile) for the cure of inherited genetic diseases;
2. Mid term: $CD34^+CD38^{int/lo}$ cells (e.g. 12-40% percentile) for a treatment duration of about 3-4 months (e.g. for microenvironment-targeted delivery of anti-cancer proteins);
3. Short term: $CD34^+CD38^{+/int}$ cells (e.g. 41-70% percentile) for a treatment duration of about 1-2 months (e.g. for microenvironment-targeted delivery of anti-cancer proteins).

In another aspect, the present invention provides a haematopoietic progenitor cell population for use in gene therapy, wherein said cells have been separated from a population of cells comprising haematopoietic stem and progenitor cells and then transduced with a nucleotide of interest.

Such haematopoietic progenitor cell gene therapy may be suited to treatment of acquired disorders, for example cancer, where time-limited expression of a (potentially toxic) anti-cancer nucleotide of interest may be sufficient to eradicate the disease.

Particularly suitable nucleotides of interest for application in haematopoietic progenitor cell gene therapy include, for example, interferon-alpha2b, other type-1 interferons, other immune-stimulating cytokines (e.g. IL-2, IL-12), apoptosis-inducing transgenes such as TNF-related apoptosis-inducing ligand (TRAIL) and tumour microenvironment-disruptive factors.

In one embodiment the haematopoietic progenitor cell population has the $CD34^+CD38^{int}$ phenotype, for example the haematopoietic progenitor cell population has been enriched for the $CD34^+CD38^{int}$ phenotype.

A population of cells with a $CD34^+CD38^{int}$ phenotype may be separated using flow cytometry methods. The $CD38^{int}$ population of haematopoietic progenitor cells may be contained in the 10-70% range of CD38 expression, as determined by flow cytometry (see, for example, Example 3 and FIG. 4—here the $CD38^{int}$ population has been further separated into $CD38^{int1}$ and $CD38^{int2}$). Haematopoietic stem cells may be contained in the 0-10% range of CD38 expression.

In another embodiment, the haematopoietic progenitor cell population has a $CD34^+CD38^{int1}$, $CD34^+CD38^{int2}$ and/or $CD34^+CD38^+$ phenotype, for example the haematopoietic progenitor cell population has been enriched for the $CD34^+CD38^{int1}$, $CD34^+CD38^{int2}$ and/or $CD34^+CD38^+$ phenotypes. Thus, for example, the progenitor cell population may substantially comprise $CD34^+CD38^{int1}$, $CD34^+CD38^{int2}$ and/or $CD34^+CD38^+$ cells.

In another embodiment the transduced progenitor cell population is administered in combination with a population of haematopoietic stem cells, for example unmodified haematopoietic stem cells. The haematopoietic stem cells may have the CD34+CD38− phenotype.

In another aspect, the present invention provides a population of cells with a CD34+CD38$^{int}$ phenotype, for example a population of cells enriched for cells with the CD34+CD38$^{int}$ phenotype, for use in gene therapy, wherein said population of cells has been transduced with a nucleotide of interest.

In another aspect, the present invention provides a population of cells with a CD34+CD38$^{int1}$, CD34+CD38$^{int2}$ and/or CD34+CD38+ phenotype, for example a population of cells enriched for cells with a CD34+CD38$^{int1}$, CD34+CD38$^{int2}$ and/or CD34+CD38+ phenotype, for use in gene therapy, wherein said population of cells has been transduced with a nucleotide of interest. Thus, for example, the progenitor cell population may substantially comprise CD34+CD38$^{int1}$, CD34+CD38$^{int2}$ and/or CD34+CD38+ cells.

In another aspect, the present invention provides a haematopoietic progenitor cell population for use in gene therapy, wherein the haematopoietic progenitor cell population has the CD34+CD38$^{int}$ phenotype (e.g. the haematopoietic progenitor cell population has been enriched for the CD34+CD38$^{int}$ phenotype) and has been transduced with a nucleotide of interest.

In another aspect, the present invention provides a haematopoietic progenitor cell population for use in gene therapy, wherein the haematopoietic progenitor cell population has the CD34+CD38$^{int1}$, CD34+CD38$^{int2}$ and/or CD34+CD38+ phenotype (e.g. the haematopoietic progenitor cell population has been enriched for a CD34+CD38$^{int1}$, CD34+CD38$^{int2}$ and/or CD34+CD38+ phenotype) and has been transduced with a nucleotide of interest. Thus, for example, the progenitor cell population may substantially comprise CD34+CD38$^{int1}$, CD34+CD38$^{int2}$ and/or CD34+CD38+ cells In another aspect, the present invention provides a method of preparing a population of haematopoietic progenitor cells for clinical use, said method comprising separating a population of haematopoietic progenitor cells from a population of cells comprising haematopoietic stem and progenitor cells, and transducing the separated cell population with a nucleotide of interest.

In one embodiment the haematopoietic progenitor cell population has the CD34+CD38$^{int}$ phenotype, for example the haematopoietic progenitor cell population has been enriched for the CD34+CD38$^{int}$ phenotype.

In another embodiment, the haematopoietic progenitor cell population has a CD34+CD38$^{int1}$, CD34+CD38$^{int2}$ and/or CD34+CD38+ phenotype, for example the haematopoietic progenitor cell population has been enriched for the CD34+CD38$^{int1}$, CD34+CD38$^{int2}$ and/or CD34+CD38+ phenotypes. Thus, for example, the progenitor cell population may substantially comprise CD34+CD38$^{int1}$, CD34+CD38$^{int2}$ and/or CD34+CD38+ cells.

Method of Treatment

It is to be appreciated that all references herein to treatment include curative, palliative and prophylactic treatment; although in the context of the present invention references to preventing are more commonly associated with prophylactic treatment. The treatment of mammals, particularly humans, is preferred. Both human and veterinary treatments are within the scope of the present invention.

Prostaglandin

Prostaglandin E2 or a prostaglandin E2 derivative may be used for increasing gene transfer efficiency when transducing haematopoietic stem or progenitor cells with a vector, preferably a viral vector.

In one embodiment of the present invention the prostaglandin E2 derivative is 16,16-dimethyl prostaglandin E2.

By derivative, it is to be understood that prostaglandin E2 is modified by any of a number of techniques known in the art, preferably to improve properties such as stability and activity, while still retaining its function of increasing gene transfer efficiency when transducing haematopoietic stem cells with a vector.

It is also envisaged that the prostaglandin E2 or prostaglandin E2 derivative may be substituted by prostaglandin receptor agonists, for example small molecule drugs acting on the EP4 receptor, in any of the aspects and embodiments described herein.

EXAMPLES

Example 1

Highly Purified HSCs are More Transducible by Lentiviral Vectors

We studied the differential effect of a microRNA on haematopoietic stem and progenitor cell populations. To this end, CD34+CD38− and CD34+CD38+ cord blood HSPCs were transduced with lentiviral miRNA sponge or overexpressing vectors (data not shown). Unexpectedly, and in contrast to what is widely assumed in the field, we noted a 1.5-fold increased gene transfer into the more primitive, CD34+CD38− HSC-enriched subset. We independently confirmed this observation on multiple cord blood and adult bone marrow donors using biologically neutral vectors expressing marker genes, demonstrating a 1.5 to 2-fold increased gene transfer efficiency into sorted CD34+CD38− HSC-enriched fractions as compared to bulk CD34+ or CD34+CD38+ cell transduction (FIG. 1(A)).

Since bulk CD34+ HSPCs contain a small subset of CD38− cells, we wanted to test whether this increased transducibility of more primitive cells was also maintained within a bulk culture, or whether pre-sorting was necessary to see this effect. We thus made a side-by-side comparison of a sort-LV protocol (first sorting of CD38 subpopulations, then lentiviral vector transduction after 24 h of pre-stimulation) with an LV-sort protocol (24 h pre-stimulation followed by lentiviral vector transduction, and sorting of CD38 subpopulations 24 h after transduction). While an increased transduction of CD38− cells was also evident in the LV-sort group, the effect was significantly greater if sorting was performed before transduction (FIG. 1(A)).

Thus, working on highly purified HSC-enriched subpopulations gives a clear advantage in terms of transduction.

Figure 1B:
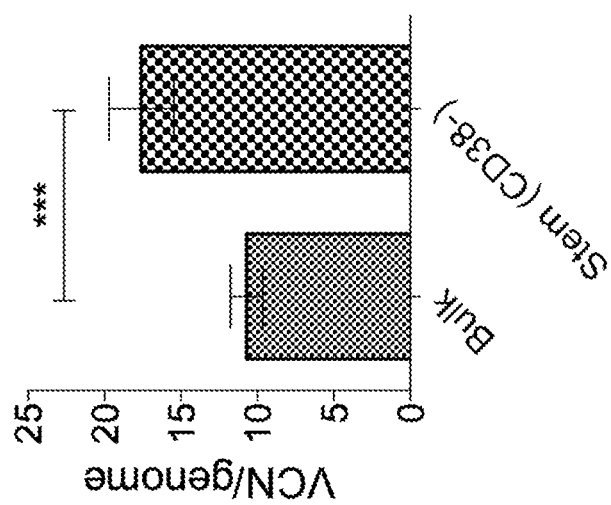

We have confirmed that the increased gene transfer into pre-purified CD34+CD38− HSPCs as opposed to bulk CD34+ cells is maintained in vivo after xenotransplantation (FIG. 1(B)). These data suggest that the effect is occurring at the level of hematopoietic stem cells, and is likely to persist long-term in patients undergoing gene therapy.

Example 2

Figure 2:
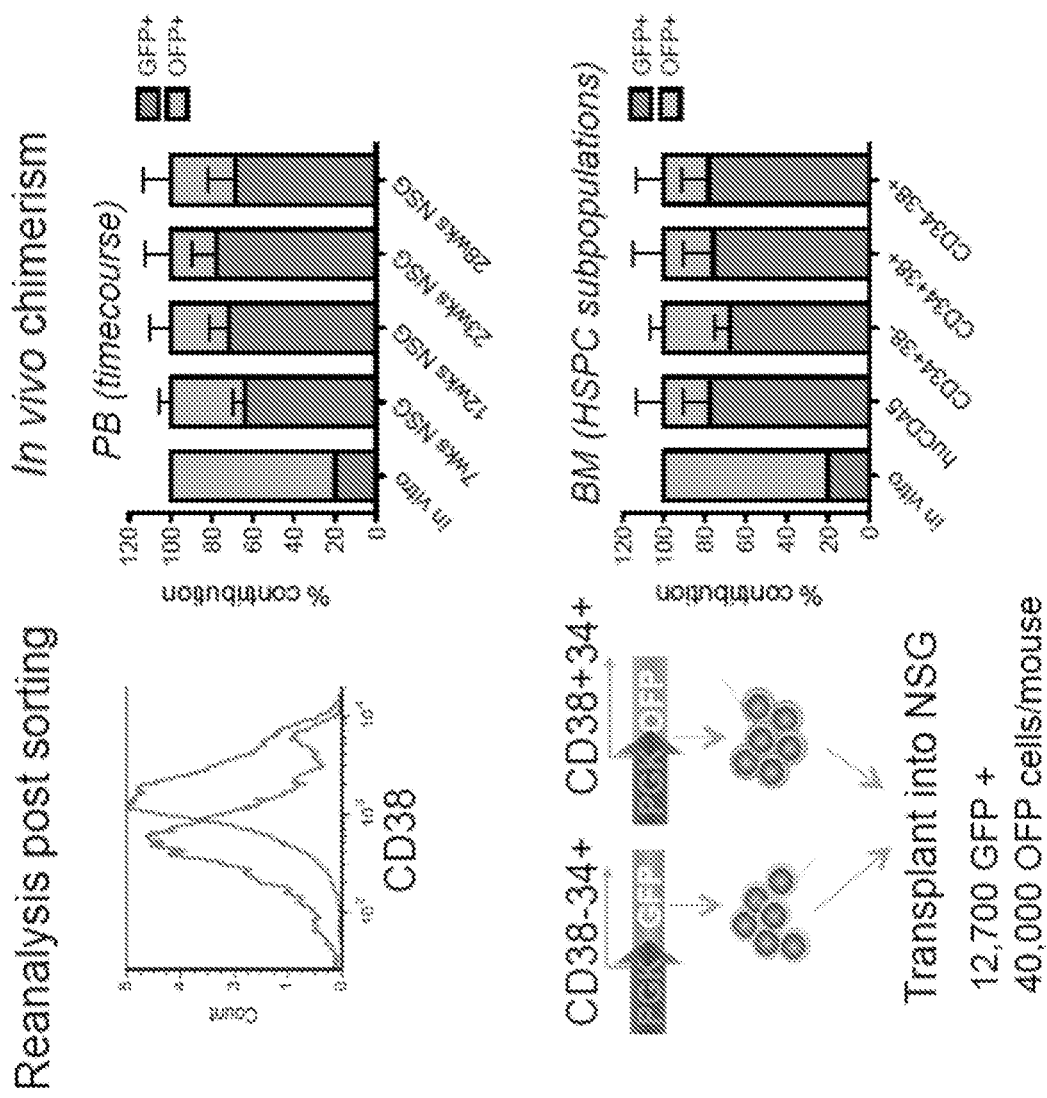

A Bead-Based, Sequential Negative/Positive Selection for CD38 and CD34, Respectively, Allows Purification of Cells with Superior NSG Engraftment Potential In order to test the feasibility of a bead-based, sequential negative/positive selection for CD38 and CD34, respectively, we applied a commercially available CD38 selection kit to human cord blood mononuclear cells and tested the engraftment potential of the CD38⁻ (further enriched for CD34 by positive selection) and CD38⁺ fraction in NSG mice by competitive transplantation (FIG. 2). Even though we used a first generation, non-optimised selection protocol, we could clearly demonstrate an engraftment advantage for the CD38⁻ fraction. While CD38⁻ cells made up less than 20% of the transplant, 70-80% of long-term engraftment was derived from this fraction, motivating further optimisation of this purification protocol.

Example 3

Modelling a Split Transplant in NSG Mice

To model the co-transplantation of genetically-modified long-term repopulating cells with short-term progenitor cells, we differentially marked the stem cell enriched fraction and various progenitor cell fractions with a set of fluorescent protein expressing lentiviral vectors (LV) and studied the engraftment kinetics in NSG mice, both in a competitive and a non-competitive setting.

First, CD34⁺ adult bone marrow HSPC were sorted into CD34⁺CD38⁻ (+/−) and CD34⁺CD38$^{hi}$ (+/hi) cells, pre-stimulated in Stem Span SFEM containing SCF (300 ng/mL), Flt3L (300 ng/mL), TPO (100 ng/mL), IL6 (60 ng/mL) and dmPGE2 (10 μM) for 16 h, and transduced with a GFP-LV (+/−) or OFP-LV (+/hi). After 24 h of transduction, cells were injected into 8 week old, sublethally irradiated NSG mice as follows:
  Group 1: 27,000+/− cells per mouse (n=3);
  Group 2: 248,000+/hi cells per mouse (n=3);
  Group 3: 27,000+/− and 248,000+/hi cells per mouse (n=3)

Figure 3:
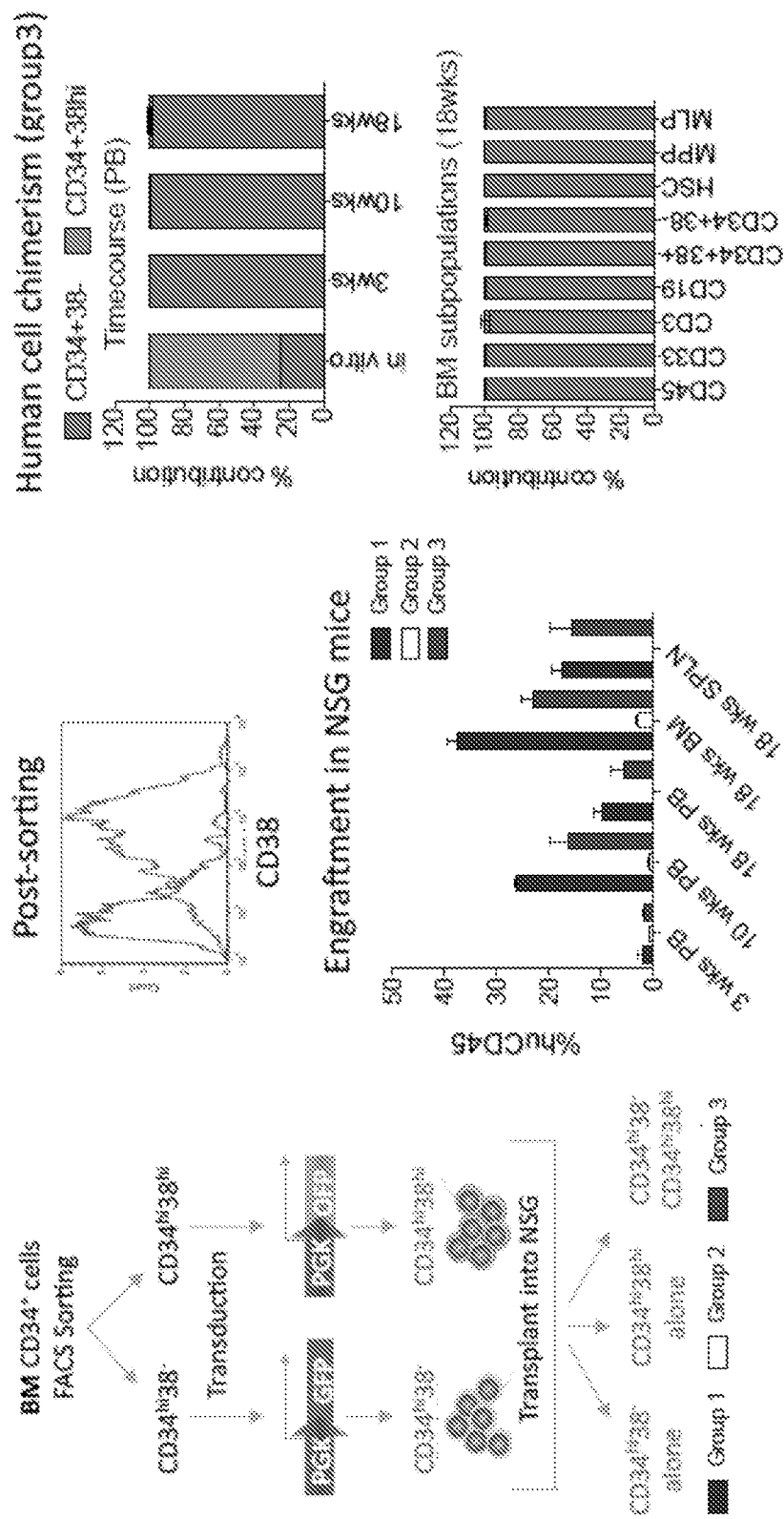

Engraftment (group 1, 2, 3) and chimerism (group 3) were monitored over time in the peripheral blood, and haematopoietic organs were analysed 18 weeks after transplantation (FIG. 3).

We found that CD34⁺/CD38$^{hi}$ cells did not engraft in the mouse, not even short term at 3 weeks post transplantation. In group 3, where we mixed OFP-positive CD34⁺/CD38$^{hi}$ cells with GFP-positive CD34⁺/CD38⁻ cells, we followed the GFP/OFP chimerism over time and in the indicated haematopoietic subpopulations (HSC: CD34⁺CD38⁻CD90⁺CD45RA⁻; MPP: CD34⁺CD38⁻CD90⁻CD45RA⁻; MLP: CD34⁺CD38⁻CD90⁻CD45RA⁺). Strikingly, the CD34⁻/CD38$^{hi}$ derived cells were almost absent during all time-points, as well as in the bone marrow and spleen (the latter not shown).

We conclude that CD34⁺/CD38⁻ cells contain most, if not all, SCID repopulating potential, short term as well as long term.

Next, we moved to CD34⁺ mobilised peripheral blood (MPB) cells (purchased from Stem Cell Technologies), since this is the preferred HSC source in adult patients where gene therapy protocol improvements are more urgently needed as compared to the paediatric setting (FIG. 4). We sorted CD34⁺ MPB into 4 subsets with increasing levels of CD38 expression (CD34⁺/CD38⁻; CD34⁺/CD38$^{int1}$; CD34⁺/CD38$^{int2}$; CD34⁺/CD38$^{hi}$), pre-stimulated these subsets in Stem Span SFEM containing SCF (300 ng/mL), Flt3L (300 ng/mL), TPO (100 ng/mL), IL6 (60 ng/mL) and dmPGE2 (10 μM) for 16 h, and transduced the subsets with the following LVs: +/−: GreenFP.LV; +/int1: CherryFP.LV; +/int2: CyanFP.LV; +/hi: OrangeFP.LV. After 24 h of transduction, cells were injected into 8 week old, sublethally irradiated NSG mice as follows:
  Group 1: 129,000+/− cells per mouse (n=6);
  Group 2: 869,000 progenitor cells (sum of +/int1, +/int2 and +/hi cells, each population contributing 33% to the progenitor mix) per mouse (n=7);
  Group 3: a mix of 129,000+/− and 869,000 pooled progenitor cells per mouse (n=6)

Engraftment (group 1, 2, 3) and chimerism (group 3) were monitored over time in the peripheral blood (FIG. 4(A)).

CD34⁺CD38$^{hi}$ (+/hi) cells showed little, but detectable engraftment potential in NSG mice at the earliest time-point, and their output extinguished thereafter. Intriguingly, the CD34⁺CD38⁻ (+/−) population from MPB showed little haematopoietic output at 3 weeks post transplantation. Instead, short term engraftment at this time-point was mostly sustained by CD34⁺CD38$^{int}$ cells (int2>int1). The contribution of the different fractions changed at 9-15 weeks post transplantation: group 1 and group 3 now showed similar levels of human CD45⁺ cell engraftment. In group 3, which was transplanted with the mix of all stem and progenitor cell populations, the CD34⁺CD38⁻ (+/−) population contributed to >70-80% of huCD45⁺ and >98% of huCD13⁺ engraftment, while the +/int1 contributed approximately 20-10% of B cells. The +/int2 and the +/hi cells did not show significant contribution to haematopoiesis at the 9 and 15 week time-points.

We conclude that the CD34⁺CD38-(+/−) cells from MPB contain most if not all long-term SCID repopulating potential, while short term repopulation is provided by CD34⁺/CD38$^{int2-high}$ (first wave) and CD34⁺/CD38$^{int1}$ cells (second wave). This provides a proof of principle that genetic modification of G-CSF-mobilised MPB derived CD34⁺CD38⁻ cells (10% of all CD34⁺ cells) is sufficient to achieve most if not all long-term engraftment by gene-modified cells. The choice whether or not to include CD34⁺/CD38$^{int}$ cells in the transduction culture is dependent on the time frame in which a take-over of haematopoiesis by transduced cells needs to be achieved. Instead, the CD34⁺/CD38$^{int2}$ cells provide short-term engraftment, and represent the ideal population to be given as uncultured, non gene-modified supporter cells to boost haematopoietic recovery after conditioning, reducing the risk of infectious and haemorrhagic complications in patients undergoing gene therapy.

Figure 4B:
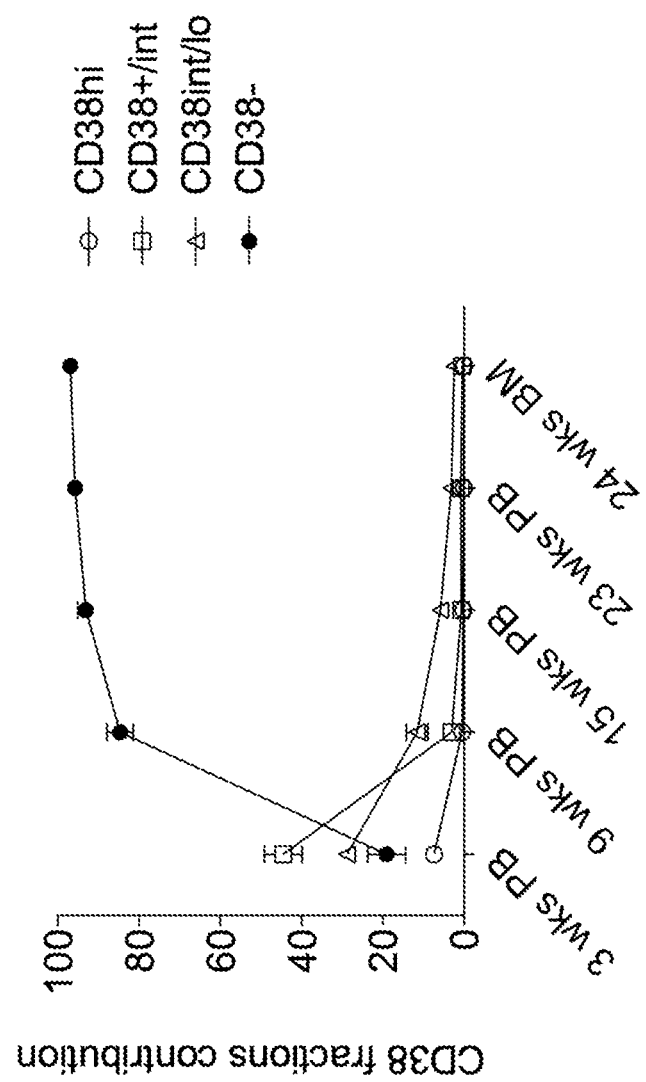

Continuing the study shown in FIG. 4(A) over a longer time period provides further insight. FIG. 4(B) shows the continuation of the study to 24 weeks, which provides a long-term readout measuring stable, HSC-derived hematopoiesis. Moreover, we have performed a replicate experiment using another mobilised peripheral blood donor and permuting the lentiviral vectors marking the CD38 fractions.

This long-term analysis confirms that >95% of long-term engraftment is derived from the CD38⁻ fraction (lowest 12% CD38 expressing cells) of cultured CD34⁺ mobilised peripheral blood HSPC. These data also underpin the engraftment kinetics of progenitor populations defined by different levels of CD38 expression: CD38$^{int/lo}$ (12-40% CD38 percentile) cells gave their highest contribution at 3 weeks with a slow decay over a 4 month time window; CD38$^{+/int}$ (41-70% CD38 percentile) cells gave their highest contribution at 3 weeks with a fast decay over a 2 month time window. CD38$^{hi}$ (71-100% CD38 percentile) cells gave low engraftment at 3 weeks.

These data now allow us to tailor the persistence of gene-modified cells:

Long term: CD34$^+$CD38$^-$ cells (0-10% percentile) for the cure of genetic diseases;
Mid term: CD34$^+$CD38$^{int/lo}$ cells (12-40% percentile) for a treatment duration of 3-4 months (e.g. for microenvironment-targeted delivery of anti-cancer proteins);
Short term: CD34$^+$CD38$^{+/int}$ cells (41-70% percentile) for a treatment duration of 1-2 months (e.g. for microenvironment-targeted delivery of anti-cancer proteins).

Example 4

Figure 6:
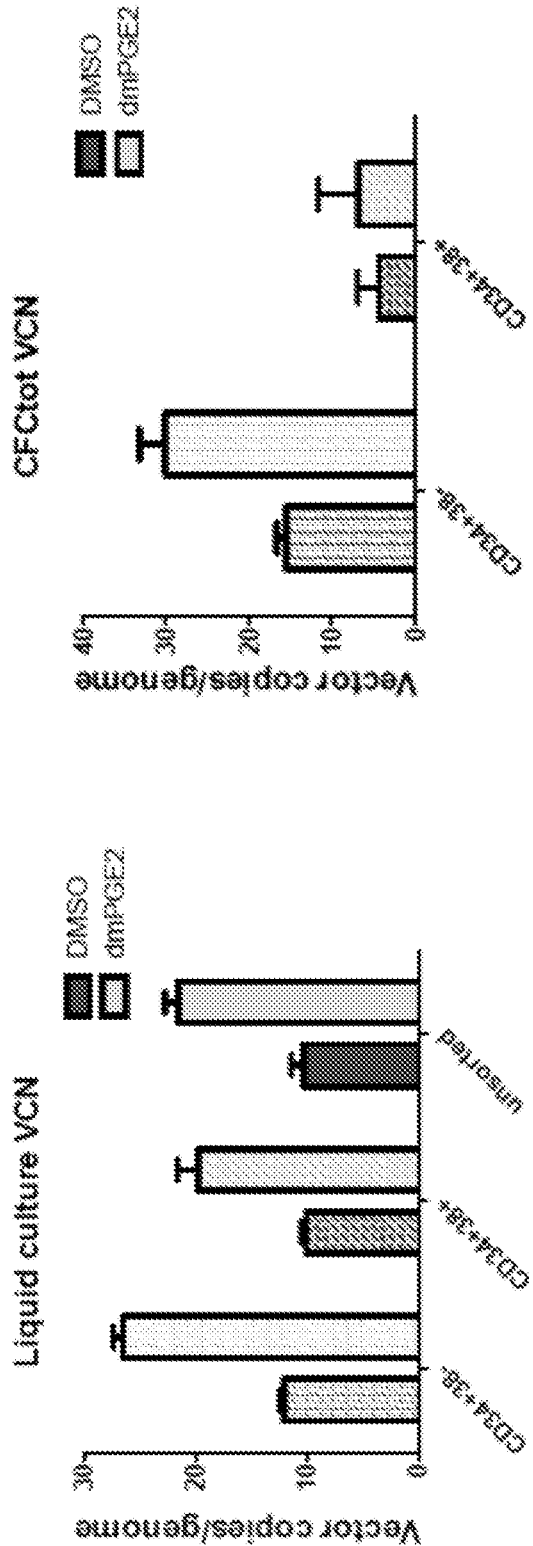

Prostaglandin E2 Increases Gene Transfer into Human Hematopoietic Stem and Progenitor Cells with NSG Repopulating Potential In an effort to exploit the anti-apoptotic properties of prostaglandin E2 (PGE2) (Pelus L M et al. Prostaglandins Other Lipid Mediat. 2011; 96:3-9), we treated CD34$^+$ HSPC exposed to stress (freeze/thaw cycles, transduction with toxic vectors, electroporation) with the long acting PGE2 homologue 16,16-dimethyl Prostaglandin E2 (dmPGE2; Cayman Chemical, Cat 14750). Unexpectedly, we found a 1.5 fold increased gene transfer efficiency into CD34$^+$ or CD34$^+$CD38$^-$ HSPC from cord blood (FIG. 5(A)) and adult bone marrow (FIG. 6) after dmPGE2 treatment. This difference in vector copy number (VCN) was maintained over more than 4 months after transplantation of the cells into NSG mice, and engraftment levels were not negatively affected by dmPGE2 treatment.

We have confirmed that G-CSF-mobilised CD34$^+$ peripheral blood stem cells also undergo more efficient transduction by lentiviral vectors if pre-stimulated with dmPGE2 (FIG. 5(B)).

In addition, we have investigated the effect of the timing of dmPGE2 stimulation on the transduction of human HSPCs by lentiviral vectors. The effect seems to be maximised when dmPGE2 is added 2 h before LV exposure (FIG. 5(C)).

Moreover, we have confirmed in an additional experiment that the increased vector copy number obtained by dmPGE2 stimulation ex vivo is maintained long term, up to 18 weeks post xenotransplantation (FIG. 5(D)).

In summary, we show here for the first time that more primitive HSC preparations are more transducible by VSVg-pseudotyped, third generation lentiviral vectors, an effect which can be further enhanced by pre-stimulation with dmPGE2. We have devised an innovative HSC gene therapy protocol, which incorporates these improvements in ex vivo manipulation. We tested this new protocol on human HSCs from cord blood, bone marrow and mobilised peripheral blood, de-convoluted for the first time the multi-lineage reconstitution kinetics of immunophenotypically defined CD34$^+$ mobilised peripheral blood populations based on quantitative differences in CD38 expression using a state-of-the-art NSG xenotransplantation model, and segregated long-term multi-lineage engrafting cells (<10% of total CD34$^+$ cells) from progenitors with rapid short-term repopulation potential. This protocol will improve safety by providing a qualitatively better gene-modified HSC fraction through improved ex vivo culture, rapid haematologic recovery sustained by uncultured progenitors and infusion of a lower integration dose into the patient. It will also improve sustainability of HSC gene therapy by allowing a substantial reduction in vector dose.

Example 5

Clinical protocol (adapted from Biffi A et al. Science 2013; 341:1233158): Total bone marrow is collected from the iliac crests under sterile conditions and using general anaesthesia, according to an internal SOP. Alternatively, patients undergo HSPC mobilisation by 5-10 µg/kg G-CSF starting from day −3, with or without a single dose of plerixaphor 6-9 h before leukapheresis. The harvested bone marrow or mobilised peripheral blood, collected in a dedicated bag, sealed and identified, is then transferred to a GMP facility. Cell purification is performed by negative/positive selection with immunomagnetic beads according to the manufacturer's procedure (Miltenyi Biotec, Bergisch-Gladbach, Germany) in GMP conditions. The purified cells are then cultured in retronectin-coated VueLife bags (American Fluoroseal, Gaithersburg, Md.) in serum-free medium supplemented with GMP-grade cytokines (see above) and exposed once or twice to GMP-grade purified vector at a multiplicity of infection of 30-100, for a total culture time of 40-60 h. At the end of the transduction procedure, the transduced CD34$^+$ cells are harvested, washed with Cell Grow medium and resuspended in saline solution at the concentration of 2-10×10$^6$ cells/mL for infusion into the patient. At the end of transduction, a fraction of the cells is collected for clonogenic assays, flow cytometry and in vitro culture, as above. Cells are kept at 4° C. up to the time of infusion, upon batch release according to Quality Control tests (results available at infusion for: viability, immunophenotype, endotoxin, large T Ag DNA, *mycoplasma*).

Example 6

Figure 7B:
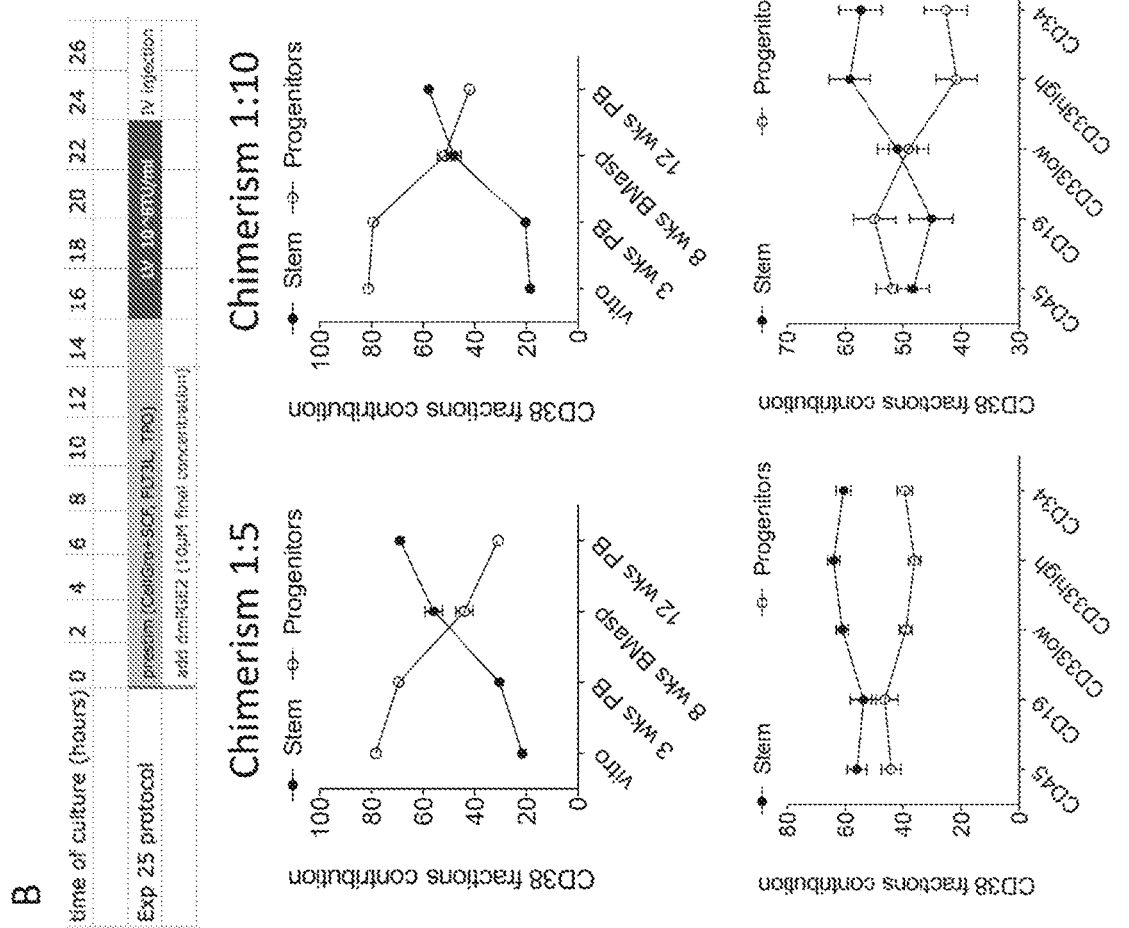

Modelling the Co-Administration of Cultured/Transduced CD34$^+$CD38$^-$ Stem Cells with Uncultured CD34$^+$CD38$^{int/+}$ Progenitor Cells The data shown in FIG. 7 relates to the combined transplantation of uncultured CD34$^+$CD38$^{int/+}$ mobilised peripheral blood progenitor cells (Progenitors) with gene-modified CD34$^+$CD38$^-$ HSPC (Stem). This experiment demonstrates that uncultured CD34$^+$CD38$^{int/+}$ (13-100% CD38 percentile) progenitors persist longer and have a higher repopulating capacity with respect to cultured/transduced CD34$^+$CD38$^{int/+}$ cells.

This means that:
1. fresh progenitors given to patients as a support population of cells will likely speed up and consolidate hematopoietic recovery in gene therapy patients, thus substantially reducing the risk of infectious and haemorrhagic complications in the first months after therapy;
2. the ratio of gene-modified stem over fresh progenitors (currently 1:8) could be adjusted in favor of the stem cells (e.g. 1:5) to improve efficient long-term gene marking;
3. part of the CD34$^+$CD38$^{int1}$ population could be removed from the support cell population to reduce competition with gene-modified CD34$^+$CD38$^-$ cells;
4. a short culture time is critical for obtaining highly functional, gene-modified HSC. Improving the functional properties of gene-modified HSC makes the interventions described in points (2) and (3) less critical as shown by similar gene-marking in CD34+ and CD33high cells in vivo both for the 1:5 and 1:10 ratio (see FIG. 7B).

Example 7

Figure 9A:
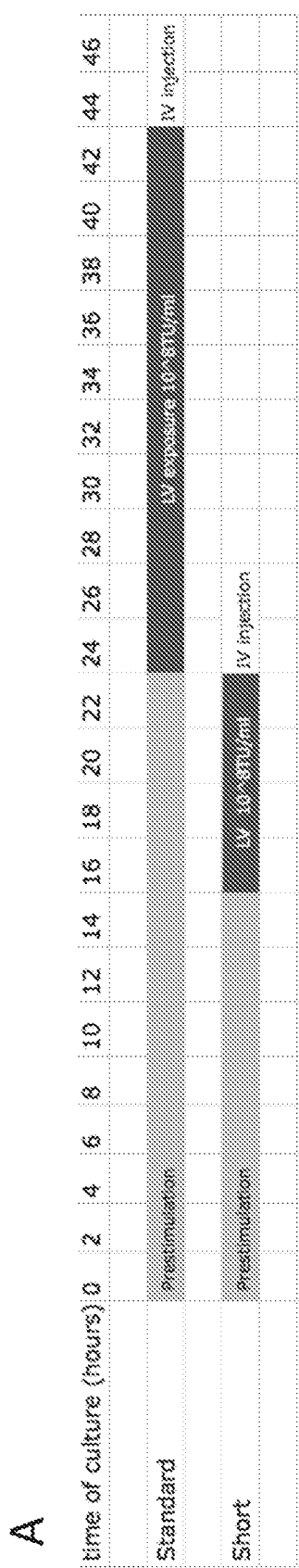
Figures 9B, 9C, 9D, 9E:
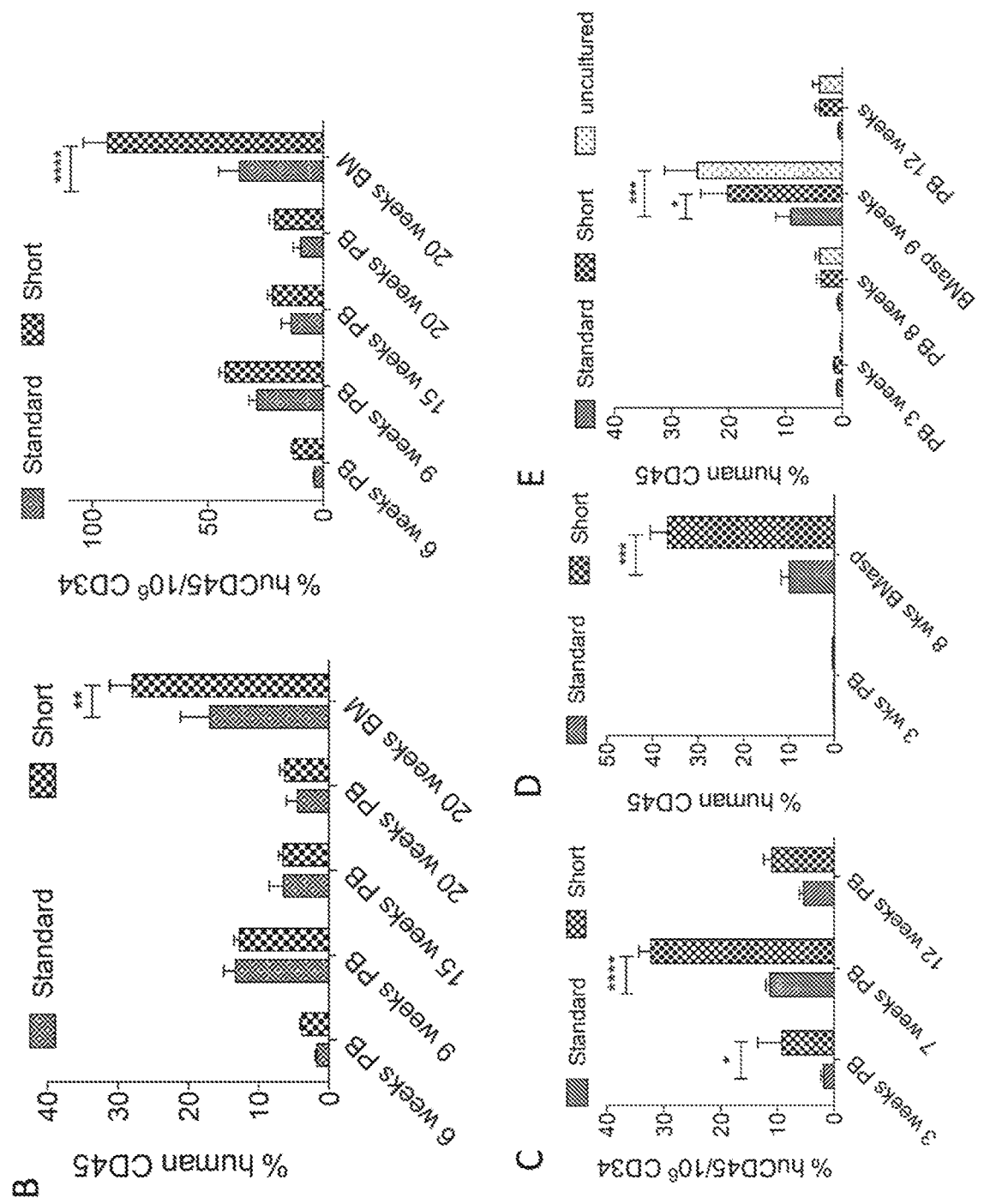

The data in FIGS. 5, 7 and 9 demonstrate that culture time negatively influences functional engraftment capacity of both stem and progenitor cells from mobilised peripheral blood. Reducing culture time to 24 h can mitigate the detrimental impact of culture and improve the quality of medicinal gene therapy products. The use of dmPGE2 allows efficient transduction of HSC in a short 24 h ex vivo manipulation protocol (FIG. 5), thus forming a strong rationale to implement this protocol in future gene therapy studies. These data also implicate that CD34 cell number, the standard measure used to dose stem cell transplants, has reduced informative value, since the CD34$^+$ cells from prolonged ex vivo cultures are not functionally equivalent to fresh CD34$^+$ cells or CD34$^+$ cells cultured for a short time period. Indeed, even though we injected less CD34$^+$ cells from the 24 h cultures with respect to the 44 h cultures, the former protocol provided higher levels of long-term engraftment.

Example 8

Figure 10:
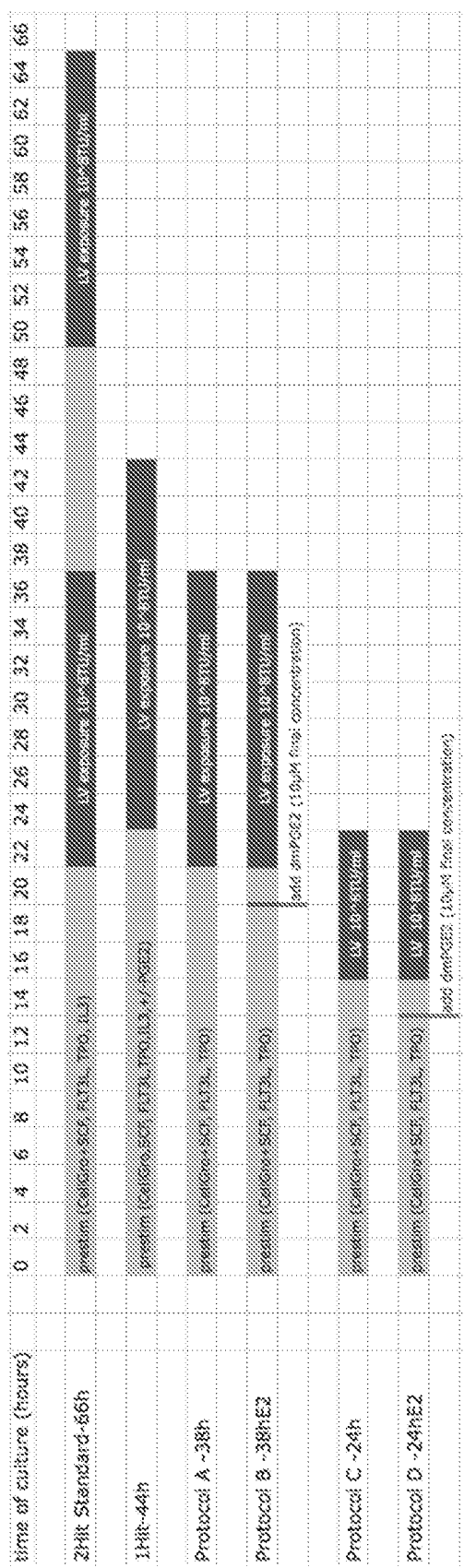

Preferred Transduction Protocols in Order to Obtain Efficient Gene Transfer into CD34$^+$CD38$^-$ HSPC from Mobilised Peripheral Blood (Mobilised with G-CSF and/or Plerixaphor or New Investigational Mobilising Agents) or Bone Marrow The protocols discussed are indicated in FIG. 10.

Reference Protocol: 2Hit Standard-66h: CD34$^+$CD38$^-$ cells transduced with the standard 2 hit protocol (66 hours), which is the current benchmark protocol for the transduction of CD34$^+$ cells (Biffi, A et al. (2013) Science 341: 1233158; Scaramuzza, S. et al. (2013) Mol. Ther. 21: 175-84).

The 1 Hit-44h protocol that we tested (see FIGS. 7 and 9) was shown to be suboptimal and will not be further pursued.

The following protocols are expected to outperform the reference and are preferable protocols for the genetic modification of CD34$^+$CD38$^-$ cells:

Protocol A: CD34$^+$CD38$^-$ cells transduced with a "single hit" protocol (38 hours) in an IL3-free medium;

Protocol B: CD34$^+$CD38$^-$ cells transduced with a "single hit" protocol (38 hours) in an IL3-free medium, with dmPGE2 exposure at 120 min pre LV exposure;

Protocol C: CD34$^+$CD38$^-$ cells transduced with a shortened "single hit" protocol (24 hours) in an IL3-free medium;

Protocol D: CD34$^+$CD38$^-$ cells transduced with a shortened "single hit" protocol (24 hours) in an IL3-free medium, with dmPGE2 exposure at 120 min pre LV exposure.

CD34$^+$CD38$^-$ cells will be purified from mobilised peripheral blood or bone marrow according to one of the technical options contemplated (e.g. microchip-based sorting or bead-based sequential selection), and plated in Culture/Transduction Medium at a density of about 10$^6$ cells/ml. Clinical grade LV (10$^7$ to 10$^8$ TU/mL, according to application) will be added at the timepoint laid out in the scheme. In Protocols B and D, dmPGE2 will be added into the culture at 120 min before LV exposure, as laid out in the scheme. At the foreseen end of the culture (see experimental scheme), cells will be washed and cryopreserved or prepared for direct patient administration (Drug product).

Environmental Conditions During MPB CD34$^+$ Cell Transduction
  Incubator
   Culture will be maintained in cell culture incubator (37° C., 5% CO2)
    Culture Dish
    Retronectin-Coated Plate or Bag
    Pre-Stimulation/Transduction Medium
     Reference Protocol: CellGro (CellGenix) medium supplemented with Penicillin/Streptomycin and SCF 300 ng/ml, FLT3L (300 ng/ml), TPO (100 ng/ml), IL3 (60 ng/ml), sterile-filtered (0.22 µm) before use.

Protocols A, B, C, D: CellGro (CellGenix) medium (or other clinical grade medium suitable for the culture of hematopoietic stem cells) supplemented with Penicillin/Streptomycin and SCF 300 ng/ml, FLT3L (300 ng/ml), TPO (100 ng/ml), sterile-filtered (0.22 µm) before use. dmPGE2 (10 µM) is added to some groups as laid out in the protocol Preferably, the drug product is infused intraosseously following suitable patient conditioning. Optionally, a suitable dose of support cells (definition of suitable dose: zero in case of non-myeloablative conditioning; in the case of myeloablative conditioning: 5×-10× the number of CD34$^+$ cells from the CD38$^+$ prep with respect to the number of CD34$^+$ cells contained in the CD38$^-$ prep, with a minimum absolute number of 2.5-3 million per kg patient weight) can be administered intravenously, preferably 1-2 days after infusion of the drug product. Alternatively, the drug product can be administrated intravenously, preferably as a co-administration with support cells.

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

The invention claimed is:

1. A method of treatment comprising administering a therapeutic cell population and a support cell population to a subject in need thereof,
    wherein the therapeutic cell population and the support cell population are prepared according to a method of preparing a therapeutic cell population and a support cell population for clinical use from a starting population of cells comprising haematopoietic stem cells, said method comprising separating a population of cells that substantially do not express CD38 but which express CD34 from the starting population of cells, and transducing the separated cell population with a vector to obtain the therapeutic cell population, wherein the separated CD38-expressing cells or portion thereof are retained to form the support cell population, and wherein the support cell population is not cultured ex vivo.

2. The method of claim 1, wherein the therapeutic cell population is administered to the subject prior to administration of the support cell population.

3. The method of claim 1, wherein the therapeutic cell population is administered to the subject contemporaneously with or simultaneously to administration of the support cell population.

4. The method of claim 1, wherein the step of transducing a population of cells with a vector comprises culturing the cells for about 12-24 hours.

5. The method of claim 1, wherein the step of transducing a population of cells with a vector comprises treating the population of cells with prostaglandin E2, or a prostaglandin E2 derivative.

6. The method of claim 5, wherein the prostaglandin E2 derivative is 16, 16-dimethyl prostaglandin E2.

7. The method of claim 5, wherein the cells are treated with prostaglandin E2 or prostaglandin E2 derivative before exposure of the cells to the vector.

8. The method of claim 1, wherein the number of CD34$^+$ cells administered to a subject in the support cell population is about 5-15× the number of CD34$^+$ cells administered in the therapeutic cell population when the subject has undergone myeloablative conditioning.

9. The method of claim 1, wherein the therapeutic and support cell populations are administered as part of an autologous stem cell transplant procedure or an allogeneic stem cell transplant procedure.

10. A method of gene therapy comprising administering a therapeutic cell population and a support cell population to a subject in need thereof,
wherein the therapeutic cell population and the support cell population are prepared according to a method of preparing a therapeutic cell population and a support cell population for clinical use from a starting population of cells comprising haematopoietic stem cells, said method comprising separating a population of cells that substantially do not express CD38 but which express CD34 from the starting population of cells, and transducing the separated cell population with a vector to obtain the therapeutic cell population, wherein the separated CD38-expressing cells or portion thereof are retained to form the support cell population, and
wherein the support cell population is not cultured ex vivo after separation from the starting population of cells.

11. The method of claim 10, wherein the therapeutic cell population has the CD34$^+$CD38$^-$ phenotype, and wherein the support cell population has the CD34$^+$CD38$^{int1}$, CD34$^+$CD38$^{int2}$, and/or CD34$^+$CD38$^+$ phenotype.

12. The method of claim 10, wherein the therapeutic cell population is administered to the subject prior to, contemporaneously with or simultaneously to administration of the support cell population.

13. The method of claim 10, wherein the number of CD34$^+$ cells administered to a subject in the support cell population is about 5-15× the number of CD34$^+$ cells administered in the therapeutic cell population when the subject has undergone myeloablative conditioning.

14. The method of claim 10, wherein the therapeutic and support cell populations are administered as part of an autologous stem cell transplant procedure or an allogeneic stem cell transplant procedure.

15. The method of claim 1, wherein the method of preparing a therapeutic cell population and a support cell population comprises the steps of:
  a. separating CD38-expressing cells from a starting population of cells comprising haematopoietic stem cells;
  b. separating CD34-expressing cells from the population of cells obtained in step (a) that do not express CD38;
  c. transducing the CD34-expressing cell population obtained in step (b) with a vector to obtain the therapeutic cell population.

16. The method of claim 1, wherein the therapeutic cell population has the CD34$^+$CD38$^-$ phenotype.

17. The method of claim 1, wherein the starting population of cells comprising haematopoietic stem cells is obtained from mobilized peripheral blood, bone marrow or umbilical cord blood.

18. The method of claim 1, wherein the CD38-expressing cells and/or CD34-expressing cells are separated using magnetic bead-based separation or flow cytometry.

19. The method of claim 1, wherein the vector is a viral vector.

20. The method of claim 19, wherein the viral vector is a lentiviral vector.

21. The method of claim 19, wherein the viral vector comprises a nucleotide of interest.

22. The method of claim 1, wherein the step of transducing a population of cells with a vector comprises culturing the cells for less than about 44 h.

23. The method of claim 1, wherein the support cell population has the CD34$^+$CD38$^{int1}$, CD34$^+$CD38$^{int2}$, and/or CD34$^+$CD38$^+$ phenotype.

* * * * *